United States Patent [19]

Gerhart

[11] 4,405,530

[45] Sep. 20, 1983

[54] PROCESS FOR PREPARING FLUORINATED AMINO-NITRILES

[75] Inventor: Fritz E. Gerhart, Kehl-Leutesheim, Fed. Rep. of Germany

[73] Assignee: Merrell Toraude et Compagnie, Strasbourg, France

[21] Appl. No.: 321,505

[22] Filed: Nov. 16, 1981

Related U.S. Application Data

[63] Continuation-in-part of Ser. No. 210,499, Nov. 26, 1980, abandoned.

[30] Foreign Application Priority Data

Aug. 20, 1981 [GB] United Kingdom ............... 8125475

[51] Int. Cl.³ .................. C07C 120/00; C07C 121/43; C07C 121/45; C07C 121/78
[52] U.S. Cl. ............................ 260/465.5 R; 549/442; 260/390; 260/465 E; 260/465.7; 548/344; 548/475; 560/38; 562/449; 562/561; 424/319
[58] Field of Search .................. 260/465 E, 465.5 R; 549/442

[56] References Cited

U.S. PATENT DOCUMENTS 4,072,698 2/1978 Hylton et al. ................... 549/349 X

OTHER PUBLICATIONS

Kharasch and Reinmuth, "Grignard Reactions of Non-Metallic Substances", (1954), pp. 1204-1223; Prentice-Hall, N.Y.

Patai, "The Chemistry of the Carbon-Nitrogen Double Bond", (1970); pp. 256-258, 266-271, 351-352; Interscience Pub.

Rappoport, "The Chemistry of the Cyano Group", (1970), pp. 276-283; Interscience Pub.

Primary Examiner—Joseph Paul Brust
Attorney, Agent, or Firm—David E. Frankhouser; Raymond A. McDonald; William J. Stein

[57] ABSTRACT

Certain α-(fluoromethyl or difluoromethyl)-α-aminoacetonitriles are prepared by treating the appropriate α-(fluoromethyl or difluoromethyl) ketimine magnesium halide with hydrogen cyanide or with an alkali metal cyanide or ammonium cyanide and a proton source. The products are useful as intermediates for making α-(fluoromethyl or difluoromethyl)-α-amino acids having pharmacological activity.

18 Claims, No Drawings

PROCESS FOR PREPARING FLUORINATED AMINO-NITRILES

This application is a continuation-in-part of copending application Ser. No. 06/210,499, filed Nov. 26, 1980, now abandoned.

This invention relates to a process for preparing fluorinated amino-nitrile compounds which are intermediates for preparing fluorinated amino acids having useful pharmacological activity.

The invention sought to be patented comprehends a process for preparing a compound of the formula:

$$\begin{array}{c} CF_pH_{3-p} \\ | \\ R-C-CN \\ | \\ NH_2 \end{array} \qquad I$$

wherein:
p is 1 or 2 and
R is:

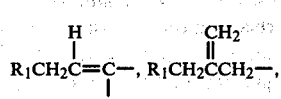

$R_2OCH_2CH_2CH_2—$, $R_2OCH_2CH_2CH_2CH_2—$, $R_3CH_2—$, or $CH_2=CHCH_2—$, wherein:
$R_1$ is hydrogen, methoxy, benzyloxy, diphenylmethoxy, triphenylmethoxy, or allyloxy;
$R_2$ is methyl, benzyl, diphenylmethyl, triphenylmethyl, or allyl; and
$R_3$ is a substituted-phenyl group of the formula:

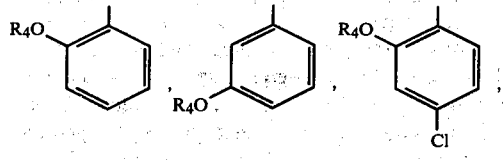

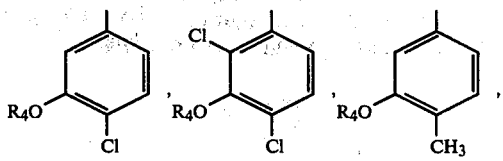

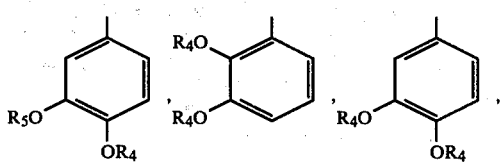

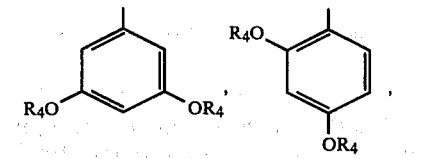

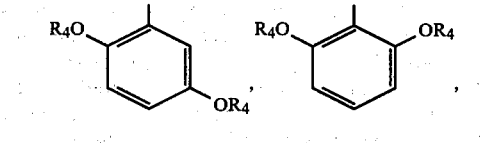

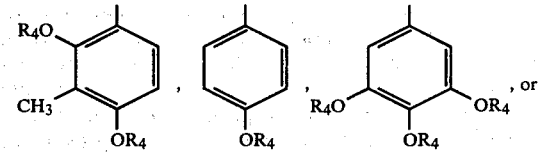

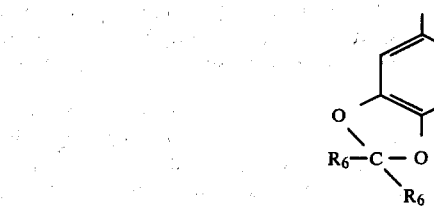

wherein $R_4$ is $C_1-C_8$ alkyl, $R_5$ is benzyl, and $R_6$ is hydrogen or methyl; with the proviso that when R is $R_3CH_2—$ wherein $R_3$ is

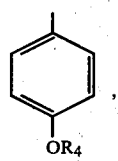

p cannot be 2;
which comprises treating a ketimine magnesium halide of the formula:

$$\begin{array}{c} CF_pH_{3-p} \\ | \\ R-C=N-MgZ; \end{array} \qquad II$$

wherein R and p have the meanings hereinabove defined and Z is chloride, bromide, or iodide; with hydrogen cyanide or with an alkali metal cyanide or ammonium cyanide and a proton source.

It is believed that the process procedes via formation of the corresponding imine of the formula:

$$R-\underset{\underset{}{|}}{\overset{CF_pH_{3-p}}{C}}=N-H \qquad III$$

wherein R and p have the meanings hereinabove defined. The imine (III) can then form the corresponding immonium ion which then reacts with the cyanide ion, or it can add hydrogen cyanide directly. Whatever the exact mechanism, the stoichemistry of the over-all process can be depicted as shown below:

$$R-\underset{\underset{}{|}}{\overset{CF_pH_{3-p}}{C}}=N-MgZ + CN^- + 2H^+ \longrightarrow R-\underset{\underset{NH_2}{|}}{\overset{CF_pH_{3-p}}{C}}-CN + MgZ^+$$

It is seen that the process requires one equivalent of the cyanide and two equivalents of the proton source. Hydrogen cyanide by itself can serve as both the proton source and the cyanide source, provided two equivalents are employed. Alternatively, the cyanide source can be an alkali metal cyanide (such as sodium cyanide or potassium cyanide), or ammonium cyanide, and the proton source can be any organic or inorganic substance of sufficient acidity to form the imine (III) from the ketimine magnesium halide (II). Weak acids, such as a water-soluble ammonium salt of a strong acid, are a preferred proton source. Ammonium chloride is especially preferred. Although strong organic or inorganic acids can be employed as the proton source, care must be taken to control the amount of acid to prevent or limit ketone formation arising from acid hydrolysis of the imine. Weak acids are preferred because hydrolysis of the imine to the corresponding ketone does not occur to any substantial extent and an excess of the weak acid can be used.

The reaction medium can be any protic or aprotic inert solvent or mixture of such solvents. By "inert solvent" is meant a solvent which is capable of substantially dissolving the reactants and which is not deleterious to the formation of the desired product. An aqueous medium is preferred. By "aqueous medium" is meant either water substantially free of other solvents or water in the presence of other compatible miscible or immiscible solvents. A suitable protic solvent can also function as the proton source.

The process can preferably be carried out at a temperature varying from about 0° C. to room temperature and a reaction time of about 30 minutes to about one hour. The temperature and time are not critical. Other temperatures and times may be employed depending upon the particular reactants and/or medium employed. The selection of the optimum reaction conditions and the reaction medium is within the skill of the art.

The ketimine magnesium halides of Formula II can be made by reaction of a Grignard reagent of the formula:

RMgZ  IV, wherein R and Z have the meanings hereinbefore defined, with fluoroacetonitrile (CH$_2$FCN) or difluoroacetonitrile (CHF$_2$CN). The Grignard reagent (IV) can be made in known manner from the corresponding organohalide (R—Z) by reaction with magnesium. The reaction of the Grignard reagent with fluoroacetonitrile or difluoroacetonitrile is carried out in a conventional manner in an aprotic solvent (for example, tetrahydrofuran or diethyl ether), at a temperature of from about −20° to −70° C., preferably −20° to −40° C. A reaction time of about 10 minutes to 12 hours (preferably 10 minutes to one hour) is employed.

The ketimine magnesium halide formed by the reaction of the Grignard reagent with fluoroacetonitrile or difluoroacetonitrile need not be isolated from its reaction mixture. Conveniently, the reaction mixture containing the ketimine magnesium halide can be added directly to the reaction medium employed for preparation of the amino-nitrile. Using this technique, whatever solvent is employed for preparing the ketimine magnesium halide will be incorporated into the medium utilized for preparation of the amino-nitrile. A preferred method is to prepare the ketimine magnesium halide in tetrahydrofuran (THF) and to add the reaction mixture thus formed directly to a water solution of hydrogen cyanide or to a water solution of an alkali metal cyanide and ammonium chloride or of ammonium cyanide. Alternatively the reaction mixture can be treated first with water (1 equivalent) before treatment with the alkali metal cyanide and ammonium chloride. It is preferable to employ a water- the ketimine magnesium halide; but immiscible solvents, such as diethyl ether, can also be used. When difluoroacetonitrile is employed as the reactant for the formation of the ketimine magnesium halide from a benzylic Grignard reagent (i.e. R$_3$CH$_2$MgX), a mixture of the desired ketimine salt and a ketimine salt side product (formed by ortho-attack by the nitrile at the benzene ring) may be produced. The desired amino-nitrile can be purified by conventional methods, such as chromatography.

The organo-halides (R—Z) employed for preparing the Grignard reagents (RMgZ) are either known compounds or can be prepared by known methods, or obvious variations thereof, from known starting materials.

The term "alkyl" when used herein means a saturated branched or straight-chain hydrocarbon radical. Examples of C$_1$-C$_8$ alkyl groups are methyl, ethyl, n-propyl, i-propyl, n-butyl, i-butyl, t-butyl, n-pentyl, n-hexyl, n-heptyl, and n-octyl. Methyl is preferred.

The fluorinated amino-nitriles of Formula I are useful as intermediates for preparing various pharmacologically or biologically active fluorinated amino acid products:

When R in Formula I is $$R_1CH_2\underset{\underset{H}{|}}{\overset{H}{C}}=C-,$$

the products are the fluorinated trans-dehydro-ornithine derivatives of Formula V:

$$H_2NCH_2-\underset{\underset{H}{|}}{\overset{H}{C}}=C-\underset{\underset{NH_2}{|}}{\overset{CF_pH_{3-p}}{C}}-CO_2H, \qquad V$$

wherein p is 1 or 2.

When R in Formula I is $R_2OCH_2CH_2CH_2$—, the products are the fluorinated ornithine derivatives of Formula VI:

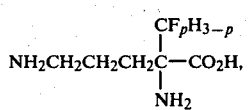

VI wherein p is 1 or 2.

When R in Formula I is —$CH_2R_3$, the products are the fluorinated 2-amino-3-(substituted)phenyl propionic acid derivatives of Formula VII:

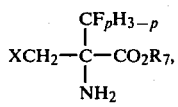

VII wherein $R_7$ is hydrogen or $C_1$-$C_8$ alkyl, p is 1 or 2, and X is a substituted phenyl group of the formula:

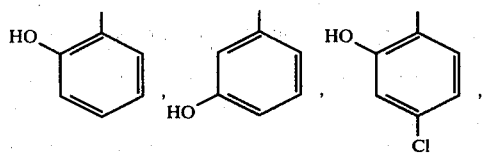

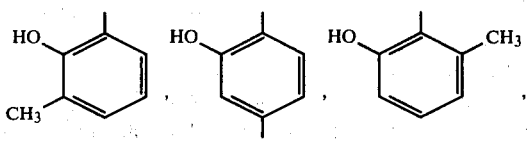

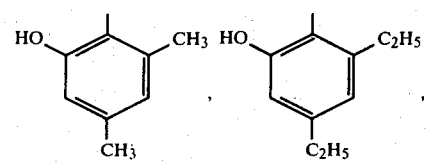

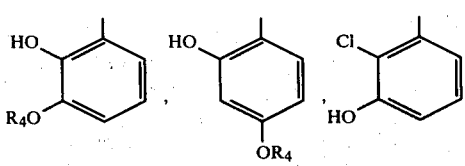

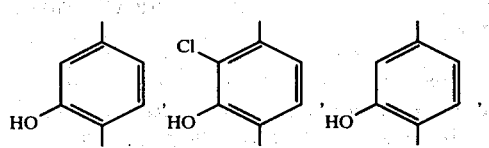

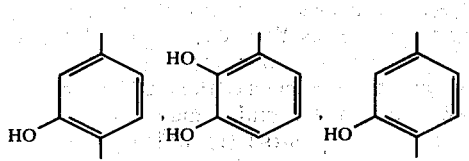

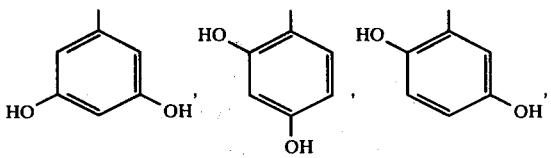

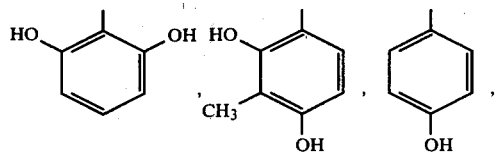

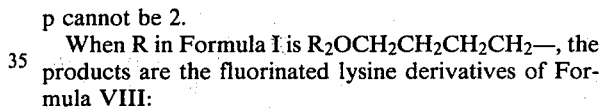

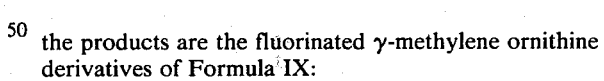

provided that when X is

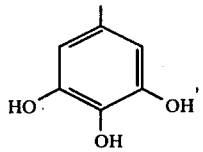

p cannot be 2.

When R in Formula I is $R_2OCH_2CH_2CH_2CH_2$—, the products are the fluorinated lysine derivatives of Formula VIII:

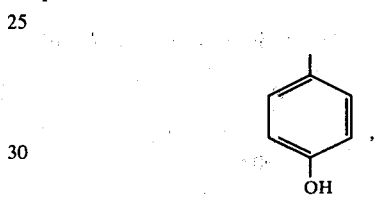

VIII wherein p is 1 or 2.

When R in Formula I is

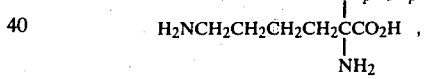

the products are the fluorinated γ-methylene ornithine derivatives of Formula IX:

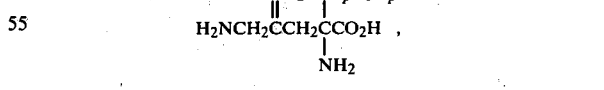

IX wherein p is 1 or 2;

or the fluorinated γ-oxo ornithine derivatives of Formula X:

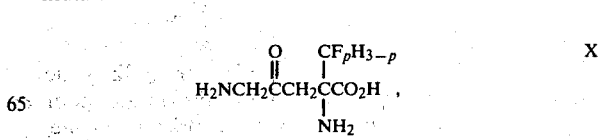

X wherein p is 1 or 2;

or the fluorinated histidine derivatives of Formula XI:

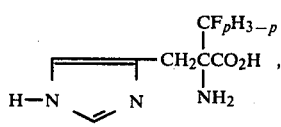

wherein p is 1 or 2.

When R in Formula I is

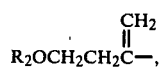

the products are the fluorinated β-methylene ornithine derivatives of Formula XII:

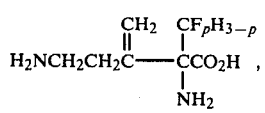

wherein p is 1 or 2;

or the β-oxo fluorinated ornithine derivatives of Formula XIII:

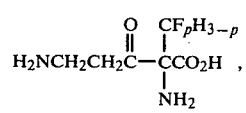

wherein p is 1 or 2.

When R in Formula I is $CH_2=CH-CH_2-$, the products are the fluorinated γ-oxo ornithine derivatives of Formula X or the histidine derivatives of Formula XI, wherein p is 1 or 2.

The fluorinated trans-dehydroornithine derivatives of Formula V can be prepared using conventional procedures according to the reaction sequence (Scheme A) depicted below:

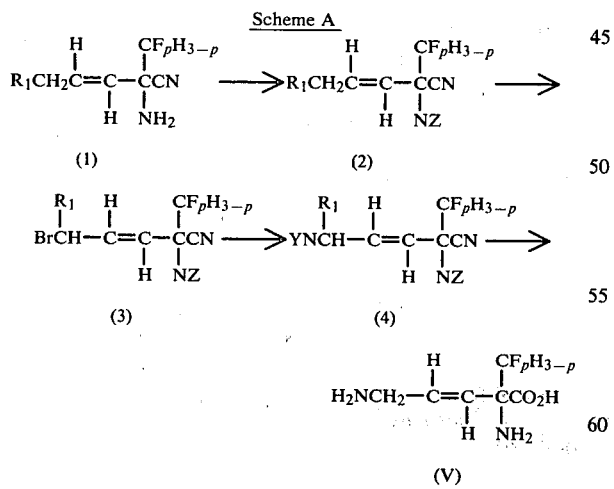

In Scheme A, $R_1$ is hydrogen, p is 1 or 2, NZ is the trifluoroacetamido group or the phthalimido group, or other suitable protecting group for a primary amine, and YN is the hexamethylenetetrammonium group or the phthalimido group.

In the first step of Scheme A, the fluorinated aminonitrile intermediate (1) is treated with trifluoroacetic anhydride or phthaloyldichloride to form the N-protected amino-nitrile (2), which then undergoes allylic bromination with N-bromosuccinimide in the presence of benzoylperoxide to afford the bromo N-protected amino-nitrile (3). Treatment of (3) with hexamethylenetetramine or an alkali metal phthalimide provides the corresponding N,N'-diprotected diamino-nitrile derivative (4) which is heated with conc. hydrochloric acid at 100° C. to simultaneously hydrolyze the nitrile groups and remove the amino protecting groups, thus affording the final product (V).

The products of Formula VI can be prepared using conventional procedures according to the reaction sequence (Scheme B) depicted below:

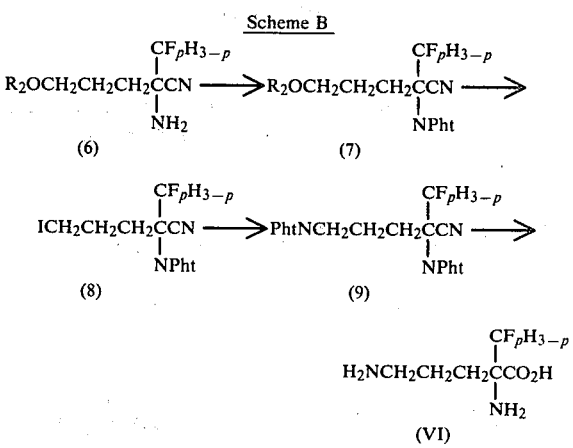

In Scheme B, $R_2$ and p have the meanings hereinbefore defined, and PhtN or NPht means the phthalimido group, which has the following structural formula:

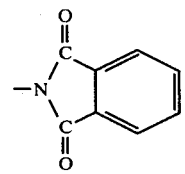

In the first step of Scheme B, the fluorinated amino-nitrile intermediate (6) is treated with phthaloyldichloride to form the N-protected amino-nitrile (7). The alkoxy group ($OR_2$) of the N-protected amino-nitrile intermediate (7) is then replaced by iodine by conventional methods. In one method, the intermediate (7) is treated with three equivalents of trimethylsilyliodide (TMSI) which affords the iodo intermediate (8) directly. In another method, the intermediate (7) is treated with TMSI (two equivalents) and then with water under which conditions the alkoxy group of intermediate (7) is cleaved to the corresponding free hydroxy group. The hydroxy intermediate thus formed is then treated with methanesulfonyl chloride to give the corresponding methanesulfonyloxy intermediate which upon treatment with sodium iodide provides the iodo intermediate (8). Treatment of the iodo intermediate (8) with an alkali metal phthalimide gives the N,N'-diprotected diamino-nitrile (9) which is heated with concentrated mineral acid (e.g. hydrochloric acid) to simultaneously hydrolyze the nitrile group and remove the N-protecting groups, thus affording the final product (VI).

The method of Scheme B can also be employed to prepare the fluorinated lysine derivatives of Formula VIII or the fluorinated β-methylene ornithine derivatives of Formula XII using as starting materials for the reaction sequence the fluorinated amino-nitriles of Formula (10) and (11), respectively:

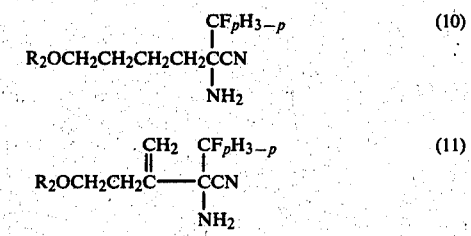

wherein $R_2$ and p have the meanings hereinbefore defined.

A modification of the method depicted in Scheme B can be employed to prepare the fluorinated trans-dehydro ornithine derivatives of Formula V or the γ-methylene derivatives of Formula IX from the respective fluorinated amino-nitrile starting materials of Formula (12) and (13), respectively:

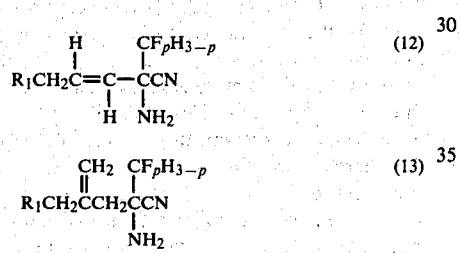

wherein $R_1$ is methoxy, benzyloxy, diphenylmethoxy, triphenyloxy, or allyloxy, and p is 1 or 2. $R_1$ is preferably methoxy. In this modification, instead of treating the N-protected amino-nitrile with TMSI, the N-protected amino-nitrile is treated with boron tribromide to form the corresponding bromo intermediate. The bromo intermediate is then used in place of the iodo intermediate in the reaction sequence of Scheme B to prepare the N,N'-diprotected diamino nitrile which is finally hydrolyzed to the desired product of Formula V or VI.

The fluorinated γ-oxo ornithine derivatives of Formula X can be prepared by conventional procedures according to the reaction sequence (Scheme C) depicted below:

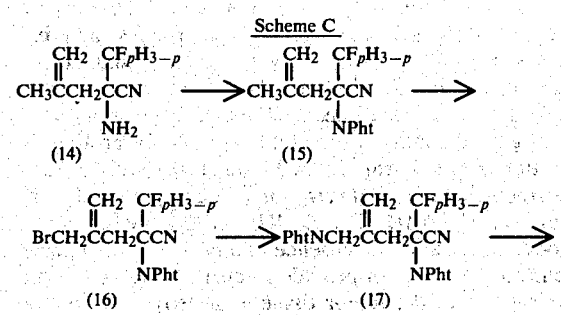

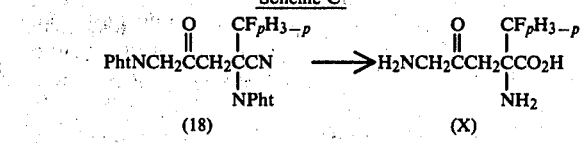

In Scheme C, PhtN, NPht, and p have the meanings as employed in Scheme B.

In the first step of Scheme C, the fluorinated amino-nitrile (14) is treated with phthaloyldichloride to afford the N-protected amino-nitrile (15). The N-protected amino-nitrile (15) is then brominated with N-bromosuccinimide in the presence of benzoyl peroxide to give the bromo N-protected amino-nitrile (16). Treatment with potassium phthalimide provides the N,N'-diprotected diamino-nitrle (17) which is oxidized with ozone to afford the γ-oxo intermediate (18). Treatment of this intermediate with concentrated hydrochloric acid at 100° C. removes both amino protecting groups and hydrolyzes the nitrile function to give the desired fluorinated γ-oxo ornithine derivative (X).

The fluorinated γ-oxo ornithine derivatives of Formula X can also be prepared by the reaction sequence (Scheme D) shown below:

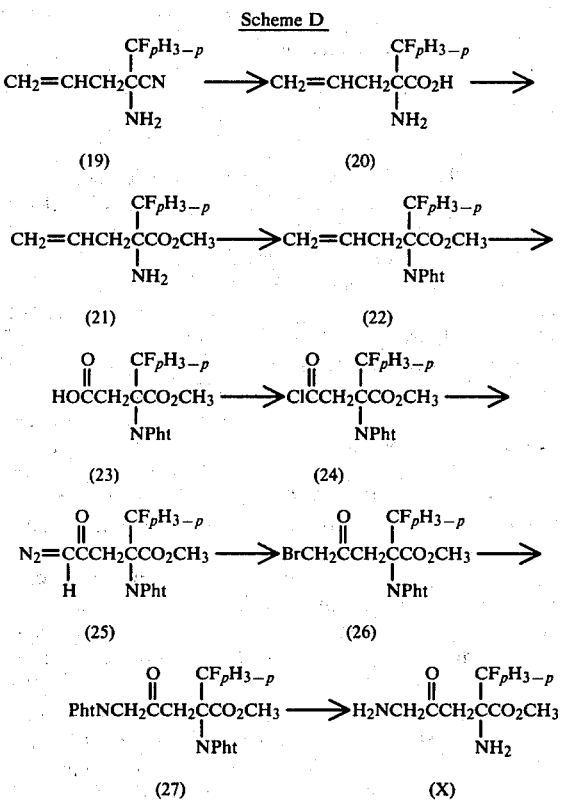

In Scheme D, PhtN, NPht, and p have the meanings as employed in Scheme B.

In the first step of Scheme D, the fluorinated amino-nitrile (19) undergoes acid hydrolysis to give the corresponding fluorinated amino acid (20) which is then esterified to give the amino-acid ester (21). Treatment of the ester (21) with phthaloyldichloride gives the N-protected amino acid ester (22). Reaction of the N-protected amino acid ester (22) with potassium permanganate oxidizes the double bond and provides the N-protected amino diacid half ester (23) which is converted to the corresponding acid chloride (24) using thionyl chloride. Reaction of the acid chloride (24) with diazomethane yields the corresponding diazoketone (25), which upon reaction with hydrogen bromide, gives the corresponding N-protected δ-bromo γ-oxo amino acid ester (26). Reaction of this intermediate with potassium phthalimide forms the N,N'-diprotected γ-oxo ornithine ester (27). Treatment of the ester (27) with hydrochloric acid at 100° C. removes the amino protecting groups and hydrolyzes the ester function to give the desired fluorinated γ-oxo ornithine derivative (X).

As will be apparent to those skilled in the art, the first two steps in the reaction sequence of Scheme D can be omitted. During the subsequent reaction sequence, the nitrile function remains intact up to the final step where it (rather than the ester function) is hydrolyzed to generate the carboxylic acid function.

The fluorinated γ-keto ornithine derivatives of Formula X can be converted to the fluorinated histidine derivative of Formula XI in two steps. The first step entails reaction with potassium thiocyanate to form the 2-mercapto-imidazole (28):

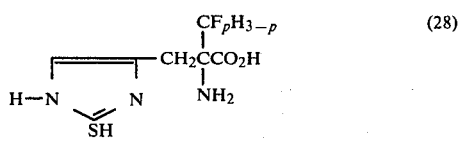

wherein p has the meaning hereinbefore defined.

In the second step, the 2-mercapto-imidizole (28) is treated with ferric chloride, which removes the —SH group, to afford the desired product (X).

The products of Formula VII wherein R is hydrogen, in general, can be prepared in known manner by direct acid hydrolysis of the amino-nitrile intermediate of Formula I wherein R is the group $R_3CH_2$—. The amino-nitrile intermediate can be hydrolyzed in one step or stepwise to give the corresponding amino acid product. In a one step process the hydrolysis can be performed using a concentrated acid, such as hydrogen bromide at 80° C. to 125° C. for about 0.5 to 24 hours, under which conditions hydrolysis of the nitrile function is also accompanied by cleavage of the alkoxy groups present in the phenyl ring. In a stepwise process the amino-nitrile intermediate is treated with a lower alcohol (e.g. methanol or ethanol) saturated with anhydrous hydrogen chloride for 1 to 24 hours, preferably 10 hours, at about 0° to 50° C., preferably 25° C., to give the corresponding amino acid amide, which can then be hydrolyzed to the amino acid by treatment with 50% aqueous sulfuric acid for about 2 to 6 hours at about 60° to 100° C., preferably 95° C. Excess sulfuric acid must be removed. Following formation of the amino acid, the alkoxy group can be removed by treatment with concentrated hydro bromic acid at elevated temperatures (such as hereinbefore described) to give the final product.

It will be recognized by those skilled in the art, that when it is desired to prepare a product of Formula VII in which the phenyl moiety contains an alkoxy group and a hydroxy group, an intermediate of Formula I wherein R is:

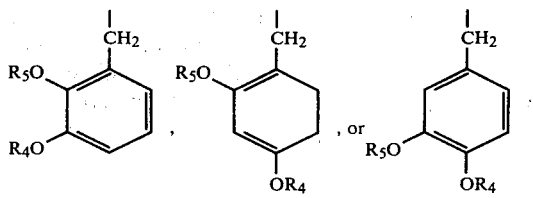

wherein $R_4$ is $C_1$-$C_8$ alkyl and $R_5$ is benzyl or trimethylsilyl, must be employed since the benzyloxy or trimethylsilyloxy group ($OR_5$) can be cleaved preferentially in the presence of the alkoxy group ($OR_4$). Using this method, the nitrile group is hydrolyzed and the benzyl or trimethylsilyl group is cleaved under conditions which do not affect the alkoxy group ($OR_4$). Conditions for carrying out such selective transformations are known in the art.

When it is desired to prepare a compound of Formula VII wherein $R_7$ is $C_1$-$C_8$ alkyl, the corresponding carboxylic acid ($R_7$ is hydrogen) can be esterified by conventional methods, such as by treating the acid with an alkanol saturated with hydrogen chloride. The methyl esters are preferred.

The fluorinated ornithine derivatives of Formula VI, the fluorinated lysine derivatives of Formula VIII, the fluorinated trans-dehydroornithine derivatives of Formula V, the fluorinated β-oxo ornithine derivatives of Formula XIII, the fluorinated β-methylene ornithine derivatives of Formula XII, the fluorinated γ-oxo ornithine derivatives of Formula X, and the fluorinated γ-methylene ornithine derivatives of Formula IX produce irreversible inhibition of ornithine decarboxylase enzyme (ODC) in vivo, and can be used systemically in general to decrease putrescine, spermidine, and/or spermine concentrations in cells undergoing rapid growth or proliferation. Because putrescine, spermidine, and/or spermine concentrations are decreased, the administration of a compound of Formula V, VI, VIII, IX, X, XII, or XIII provides a method for controlling undesirable cell growth or proliferation in mammals. The compounds are useful pharmacological agents for treating those diseases or conditions that are known in the art to be characterized by rapid cell growth or proliferation associated with high ODC activity. In particular, the compounds are useful systemically for controlling the growth of tumor tissues in mammals and for controlling the growth of pathogenic parasitic protozoa in infected domestic animals and humans. The compounds can also be employed to study the presence and physiological function of ODC inhibition in biological system and its relationship to pathological processes.

As used herein, the term "tumor tissue" means both benign and malignant tumors or neoplasms, and includes melanomas, lymphomas, leukemias, and sarcomas. The term "controlling the growth of tumor tissue", as used herein, means slowing, interrupting, arresting, or stopping the growth of a rapidly proliferating tumor in a warm blooded animal. It should be understood that the administration of a compound of Formula V, VI, VIII, IX, X, XII, or XIII to a warm blooded animal in the absence of a cancer chemotherapeutic agent does not provide a "cure" for the tumor in the sense that the tumor tissue is destroyed or totally eliminated from the body of the animal being treated.

For controlling the growth of tumor tissue, a compound of Formula V, VI, VIII, IX, X, XII, or XIII can be administered to the patient in conjunction with other therapeutic methods or in combination with cytotoxic drugs known in the art to be useful for cancer chemotherapy. For example, the compound can be administered in conjunction with surgical excision of the tumor or with radiation therapy, hormonal treatment, immunotherapy, or local heat therapy. Moreover, in a preferred manner, the compound can be administered to a patient in combination with a chemical cytotoxic agent known in the art to be useful for tumor chemotherapy. When such combination therapy is employed for the treatment of a tumor, the cancer chemotherapeutic agent may be administered at a dosage known in the art to be effective for treating the tumor. However, the compound may produce an additive or synergistic effect with a chemotherapeutic agent against a particular tumor. Thus, when such combination antitumor therapy is used, the dosage of the chemotherapeutic agent administered may be less than that administered when the agent is used alone. In combination with the compound, the chemotherapeutic agent may, therefore, be administered at a lower dosage level or at less frequent intervals as compared to the chemotherapeutic agent when used alone.

In combination with a compound of Formula V, VI, VIII, IX, X, XII, or XIII, any cancer chemotherapeutic agent may be employed. Drugs commonly used for cancer chemotherapy are described in *The Medical Letter*, Vol. 22, No. 24 (Issue 571), Nov. 28, 1980, published by the Medical Letter, Inc., New Rochelle, N.Y., 10801. Illustrative examples of cytotoxic chemotherapeutic agents are: cyclophosphamide, methotrexate, prednisone, 6-mercaptopurine, procarbazine, daunorubicin, vincristine, vinblastine, chlorambucil, cytosine arabinoside, 6-thioguanine, thio-TEPA, 5-fluorouracil, 5-fluoro-2-deoxyuridine, 5-azacytidine, nitrogen mustard, 1,3-bis(2-chloroethyl)-1-nitrosourea (BCNU), (1-(2-chloroethyl)-3-cyclohexyl-1-nitrosourea) (CCNU), busulfan, adriamycin, bleomycin, vindesine, cycloleucine, or MGBG. Other cancer chemotherapeutic agents will be apparent to those skilled in the art.

The effect of the compounds of Formula V, VI, VIII, IX, X, XII, or XIII for the control of the growth rate of rapidly proliferating tumor tissue can be assessed in standard animal tumor models after oral or parenteral administration. For example, the antitumor effects can be demonstrated in the following models: (a) L1210 leukemia in mice, (b) EMT6 tumor in Balb/C mice, (c) 7,12-dimethylbenzanthracene-induced (DMBA-induced) mammary tumor in rats, or (d) Morris 7288 C or 5123 hepatoma in Buffalo rats. In addition, the antitumor effects of the compounds in combination with chemotherapeutic agents can be demonstrated in animal models. In general, in animal tumor models, the compounds of Formula V, VI, VIII, IX, X, XII, or XIII effectively reduce tumor growth rate systemically at a daily dose of from about 20 mg/kg to about 100 mg/kg (body weight). As will be apparent to those skilled in the art, the effective dosage will vary depending on the compound employed, the nature and severity of the particular neoplasm being treated, the route of administration, and the species being treated. Treatment should be initiated at lower doses, the dosage thereafter being increased until the desired effect on tumor growth is achieved.

When, in the treatment of a malignant neoplastic disease, a compound of Formula V, VI, VIII, IX, X, XII, or XIII is administered in combination with a chemotherapeutic agent, the therapeutic effect of the chemotherapeutic agent may be potentiated in that the remission produced by the chemotherapeutic agent may be enhanced and regrowth of the tumor tissue may be slowed or prevented. Use of such combination therapy therefor allows smaller doses or fewer individual doses of the chemotherapeutic agent to be employed. Thus, the detrimental and/or debilitating side effects of the chemotherapeutic agent are minimized while, at the same time, the antitumor effects are enhanced. The term "combination therapy" contemplates the administration of the compound immediately prior to the beginning of chemotherapy, concommitantly with chemotherapy, or during the period of time immediately following cessation or discontinuance of chemotherapy. Preferably, the patient is treated with the compound for about 1 to 14 days, preferably 4 to 14 days, prior to the beginning of chemotherapy, and, thereafter, on a daily basis during the course of such therapy. Daily treatment with the compound can be continued for a period after the last dose of the chemotherapeutic agent is administered.

When chemotherapy results in remission of the tumor and all tumor cells are not destroyed, regrowth of the tumor may be prevented or slowed indefinitely by continued treatment with a compound of Formula V, VI, VIII, IX, X, XII, or XIII. Thus, the compound can be administered to stop or slow the growth of the tumor during the periods when chemotherapy using a cytotoxic agent may be temporarily discontinued.

A preferred cytotoxic agent for combination therapy is methylglyoxal bis (guanylhydrazone), (MGBG), which is also an inhibitor of S-adenosyl methionine decarboxylase.

Suitable dosages of the compounds of Formula V, VI, VIII, IX, X, XII, or XIII for use in combination therapy with MGBG or other cancer chemotherapeutic agents can be any amount effective in inhibiting polyamine biosynthesis sufficiently to control the tumor growth rate or to achieve a heightened response to the cytotoxic agent administered in conjunction therewith.

The term "controlling the growth of pathogenic parasitic protozoa" means slowing, arresting, or stopping the replication of the protozoa in an infected host. The compounds of Formula V, VI, VIII, IX, X, XII, or XIII are particularly useful against *T.b. brucei* (which causes trypanosomiasis in cattle), *T.b. rhodesiense* (which causes human sleeping sickness), the coccidia, for example, *Eimeria tenella* (which causes intestinal coccidiosis in fowl (e.g. chickens, turkeys, and ducks)), and the exoerythrocytic form of the Plasmodia, for example, *Plasmodium falciparum* (which causes human malaria).

The antiprotozoal activity of the compounds can be demonstrated in vivo or in vitro in standard microbiological test procedures. For example, the activity of the compounds against *T.b. brucei* and *T.b. rhodesiense* can be determined in infected mice by administering the test compound ad lib daily (3 to 15 days post infection) as a solution in the drinking water at a concentration of 0.5 to 2%. Activity is indicated by an increase in survival time (as compared to untreated controls) or by the absence of parasites in the blood. The activity of the compounds against the coccidia can be determined in infected chickens for example, those infected with *E. tenella* by administering the test compound daily ad lib. (from the one day preinfection to 5 days post infection)

as a solution in the drinking water at a concentration of 0.5 to 2%. The cecal lesions are evaluated by a standard lesion scoring procedure. [See Reid. *Am. J. Vet. Res.*, 30, 447 (1969) and *Avian Coccidiosis*, P. Long. Editor, British Poultry Science, Ltd., Edinburgh].

The activity of the compounds against malaria (*P. falciparum*) can be determined by a standard in vitro plate culture test [See K. Rieckmann et al., *Lancet*, 1, 22 (1978)] Antimalaria activity can also be determined in special strains of mice infected with the exoerythrocitic form of *P. berghei*. In this test, the compound is administered ad lib. in drinking water at a concentration of from 0.2 to 1.0% starting two days pre-infection and continuing 28 days post-infection. Activity is measured by a significant decrease in deaths as compared to controls or by a significant increase in survival time.

The compounds of Formula V, VI, VIII, IX, X, XII, XIII, XIV$_a$, and XIV$_b$ are also capable of interrupting embryogenesis in female mammals when administered systemically. Thus, the compounds are useful as contragestational agents in female mammals when it is desired to terminate early pregnancy. The contragestational activity of the compounds can be demonstrated in mice by the method of J. Fozard, *European Journal of Pharmacology*, 65, 379 (1980). When tested by the aforesaid method, 2-fluoromethyl-2,5-diamino-3-(E)-penten-1-oic acid inhibited gestation at a dose of 80 mg/kg (body weight) administered by the S.C. route every six hours on the 8th day of gestation, as evidenced by a significant decrease in the number of viable feti per gravid female as compared to controls. In general, an effective daily dose of the compounds for terminating pregnancy in warm blooded mammals is from 10 mg/kg to 1 g/kg, preferably 10 to 100 mg/kg, administered after fertilization during the period between Standard Stages 8–16 of gestation as defined by E. Wischi [See Tables 26–27, pages 82–92, *Biology Data Book*, Altman and Dittmer, Editors, Published by the Federation of American Societies for Experimental Biology, Washington, D.C., 1964.] the period of treatment will vary with the species. In humans, the period of treatment will extend from the 6th–7th day of gestation to the 27th day.

Compounds of Formula V, VI, VIII, IX, X, XII, or XIII may have one or more additional uses, for example to treat epidermal hyperplasia (e.g. psoriasis) or prostatic hypertrophy.

The compounds of Formula V, VI, VIII, IX, X, XII, or XIII can be administered in various manners to achieve the desired antiproliferative effect. The amount of compound administered will vary and can be any effective amount. Depending upon the patient, the condition being treated and the mode of administration, the effective dosage of the compound administered may vary from about 5 mg/kg to about 100 mg/kg, of body weight of the patient per day. Unit doses of these compounds can contain, for example, from about 10 to 300 mg of the compounds and may be administered, for example, from 1 to 4 times daily.

The fluorinated ornithine derivatives of Formula VI and the fluorinated lysine derivatives of Formula VIII are describe in Belgium Pat. No. 868,882, granted July 31, 1978. Many scientific papers have been published to described DFMO and its pharmacological activity.

Preferred compounds having ODC inhibitory activity are:
2-fluoromethyl-2,5-diaminovaleric acid
 (α-fluoromethylornithine or MFMO),
2-difluoromethyl-2,5-diaminovaleric acid
 (α-difluoromethylornithine or DFMO),
2-fluoromethyl-2,6-diaminohexanoic acid
 (α-fluoromethyllysine),
2-difluoromethyl-2,6-diaminohexanoic acid
 (α-difluoromethyllysine),
2-fluoromethyl-2,5-diamino-3-(E)-pentene-1-oic acid
 (α-fluoromethyl-trans-dehydroornithine),
2-difluoromethyl-2,5-diamino-3-(E)-pentene-1-oic acid
 (α-difluoromethyl-trans-dehydroornithine),
2-fluoromethyl-2,5-diamino-4-oxo-pentanoic acid,
2-difluoromethyl-2,5-diamino-4-oxo-pentanoic acid.

The compounds of Formula VII produced irreversible inhibition of AADC enzyme in vivo and are, in particular, useful for the treatment of Parkinson's syndrome when administered in combination with exogenous dopa, in particular L-dopa. The co-administration of a compound of Formula VII with L-dopa potentiates the effect of L-dopa and thereby provides effective therapy of Parkinsonism using substantially lower doses of L-dopa resulting in a decrease in side effects. The compounds of Formula VII potentiate L-dopa by preventing its peripheral decarboxylation to dopamine, thereby increasing the circulating amount of exogenous L-dopa available for absorption into the brain and subsequent conversion there to dopamine.

In order to potentiate the therapeutic effects of L-dopa in the treatment of Parkinsonism, the dosage of a compound of Formula VII must be effective to block the decarboxylation of exogenous L-dopa peripherally, preferably without substantially blocking the decarboxylation of dopa or 5-HTP centrally. The effective dosage will vary according to the potency of the particular compound, the relative amount of co-administered L-dopa, the general health of the subject being treated, and the severity of the condition being treated. Therapy should be initiated at lower dosages, the dosage thereafter being increased until the desired potentiation of L-dopa is achieved.

When employed to treat Parkinson's syndrome alone, L-dopa is administered initially at a dose of from 0.1 to 1 g daily, after which the amount administered is gradually increased over a 3 to 7 day period to a maximum tolerated daily dose of about 8 grams (given in divided doses). By co-administering a compound of Formula VII with L-dopa, the dosage of L-dopa administered can be reduced 2–10 fold, as compared to the dosage of L-dopa alone. In general, the amount of the compound of Formula VII as compared to the amount of L-dopa administered will vary from about 1:2 to 1:500. For example, in human subjects 2-amino-2-difluoromethyl-3-(3,4-dihydroxyphenyl)propionic acid (α-difluoromethyl dopa or "DFMD") given orally at a dose of 10, 20 and 50 mg concomitantly with exogenous L-dopa at a dose of 100 mg produced a significant dose related increase in the availability of circulating L-dopa in plasma.

It will be understood that a compound of Formula VII can be co-administered with L-dopa either substantially at the same time as or prior to the administration of L-dopa. When administered prior, the compound can be given up to 4 hours prior, depending on the route of administration and severity of the condition being treated.

When used in combination with exogenous L-dopa, a compound of Formula VII can be administered in unit dosage form, either in formulations containing the compound as the sole active agent or in formulations containing both the compound and L-dopa as active agents. In either mode of administration, the amount of compound of Formula VII administered as compared to the amount of L-dopa administered, will vary from 1:1 to 1:500, depending upon the compound employed.

The compounds of Formula VII are also useful in combination with 5-HTP in the treatment of psychoneurotic depression and action myoclonus, diseases which are associated with low central levels of 5-HT.

Especially preferred compounds of Formula VII are:
2-amino-2-fluoromethyl-3-(3,4-dihydroxyphenyl)propionic acid; (monofluoromethyl dopa, "MFMD"),
2-amino-2-fluoromethyl-3-(2,5-dihydroxyphenyl)propionic acid,
2-amino-2-fluoromethyl-3-(2,3-dihydroxyphenyl)propionic acid,
2-amino-2-difluoromethyl-3-(3,4-dihydroxyphenyl)propionic acid; ("difluoromethyldopa", "DFMD"),
2-amino-2-fluoromethyl-3-(4-hydroxyphenyl)-propionic acid, methyl ester; ("monofluoromethyl-p-tyrosine methyl ester").
2-amino-2-fluoromethyl-3-(3-hydroxyphenyl) propionic acid.

The compounds of Formula VII are described in Belgian Pat. No. 868,881, granted July 31, 1978, and Belgian Pat. No. 882,105 granted March 31, 1980.

For a discussion of the biochemical and pharmacological effects of DFMD and MFMD see: M. Jung et al., *Life Sciences*, 24, 1037 (1979); J. Fozard, *J. Cardiovascular Pharmacology*, 2, 229 (1980); M. Palfreyman, *J. Neurochemistry*, 31, 927 (1978); M. Jung et al. in *Enzyme Inhibitors as Drugs*, M. Sandler, Ed., The Macmillan Press Ltd., London, 1980, pages 107–112; M. Palfreyman et al. in *Enzyme-Activated Irreversible Inhibitors*.

The compounds of Formula XI produce irreversible inhibition of histidine decarboxylase in vivo, and can be used in general to block histimine biosynthesis in mammals. The compounds of Formula XI are useful pharmacological agents for decreasing the concentrations of histamine in mammals and for the treatment of diseases or conditions characterized by excessive histamine levels. For example, the compounds can be employed for treating allergic conditions and gastric hypersecretory states. The compounds of Formula XI are described in Belgian Pat. No. 869,322 granted Aug. 14, 1978.

Preferred examples of fluorinated amino-nitriles of Formula I that can be made by the process of this invention are:
2-fluoromethyl-2-amino-5-methoxy-pentanenitrile,
2-difluoromethyl-2-amino-5-methoxy-pentanenitrile,
2-fluoromethyl-2-amino-5-benzyloxy-pentanenitrile,
2-difluoromethyl-2-amino-5-benzyloxy-pentanenitrile,
2-fluoromethyl-2-amino-3-(E)-pentenenitrile,
2-difluoromethyl-2-amino-3-(E)-pentenenitrile,
2-fluoromethyl-2-amino-5-methoxy-3-(E)-pentenenitrile,
2-difluoromethyl-2-amino-5-methoxy-3-(E)-pentenenitrile,
2-fluoromethyl-2-amino-6-methoxyhexanenitrile,
2-difluoromethyl-2-amino-6-methoxyhexanenitrile,
2-fluoromethyl-2-amino-6-benzyloxyhexanenitrile,
2-difluoromethyl-2-amino-6-benzyloxyhexanenitrile,
2-fluoromethyl-2-amino-4-methyl-4-pentenenitrile,
2-difluoromethyl-2-amino-4-methyl-4-pentenenitrile,
2-fluoromethyl-2-amino-4-methoxymethyl-4-pentenenitrile,
2-difluoromethyl-2-amino-4-methoxymethyl-4-pentenenitrile,
2-fluoromethyl-2-amino-4-pentenenitrile,
2-difluoromethyl-2-amino-4-pentenenitrile,
2-fluoromethyl-2-amino-5-hexenenitrile,
2-difluoromethyl-2-amino-5-hexenenitrile,
2-fluoromethyl-2-amino-3-methoxyethyl-3-butenenitrile,
2-difluoromethyl-2-amino-3-methoxyethyl-3-butenenitrile,
2-fluoromethyl-2-amino-3-benzyloxyethyl-3-butenenitrile,
2-difluoromethyl-2-amino-3-benzyloxyethyl-3-butenenitrile,
2-amino-2-fluoromethyl-3-(3,4-dimethoxyphenyl)propionitrile,
2-amino-2-difluoromethyl-3-(3,4-dimethoxyphenyl)propionitrile,
2-amino-2-fluoromethyl-3-(2,3-dimethoxyphenyl)propionitrile,
2-amino-2-fluoromethyl-3-(2,5-dimethoxyphenyl)propionitrile,
2-amino-2-fluoromethyl-3-(4-methoxyphenyl)propionitrile,
2-amino-2-fluoromethyl-3-(3-methoxyphenyl)propionitrile,
2-amino-2-fluoromethyl-3-(2-methoxyphenyl)propionitrile.

The pharmacologically active compounds can be administered in various manners to achieve the desired effect. The compounds can be administered alone or in the form of pharmaceutical preparations either orally or parenterally, for example, subcutaneously, intravenously, or intraperitoneally.

The amount of novel compound administered will vary and can be any effective amount. Depending on the patient, the nature or severity of the condition being treated and the mode of administration, the quantity of novel compound administered may vary over a wide range to provide an effective amount in a unit dosage form.

The solid unit dosage forms can be of the conventional type. Thus, the solid form can be a capsule which can be of the ordinary gelatin type containing a novel compound of this invention and a carrier, for example, lubricant and inert fillers such as lactose, sucrose and corn starch. In another embodiment, the novel compounds are tableted with conventional tablet bases such as lactose, sucrose or corn starch in combination with binders such as acacia, corn starch or gelatin, disintegrating agents such as corn starch, potato starch, or alginic acid, and a lubricant such as stearic acid, or magnesium stearate.

For parental administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal vegetable or synthetic origin, for example, peanut oil, soybean oil, and mineral oil. In general watern saline, aqueous dextrose, and related sugar solutions, ethanols and glycols such as propylene glycol or polyethylene glycol are preferred liquid carriers, partiularly for injectable solutions.

For use as aerosols the novel compounds in solution or suspension may be packaged in a pressurized aerosol container together with a gaseous or liquified propellant, for example, dichlorodifluoromethane, dichlorodifluoromethane with dichlorodifluoroethane, carbon dioxide, nitrogen or propane, with the usual adjuvants such as cosolvents, and wetting agents, as may be necessary of desirable. The compounds may also be administered in a non-pressurized form such as in a nebulizer or atomizer.

The intermediates of Formula I and the products derived therefrom can be prepared by various procedures which will be described individually below:

EXAMPLE 1

2-Fluoromethyl-2,5-diamino-3-(E)-pentene-1-oic acid, (α-fluoromethyl-β-trans-dehydroornithine)

A. 2-Fluoromethyl-2-amino-3-pentenenitrile (cis/trans)

Under an atmosphere of nitrogen, propenyl magnesium bromide is prepared from magnesium turnings (9.8 g, 400 mmol), freshly distilled 1-bromo-1-propene (24.2 g, 200 mmol) and 200 ml of dry tetrahydrofuran. After removing the Grignard solution from the excess of magnesium and cooling to −40° C., fluoroacetonitrile (11.8 g, 200 mmol) in tetrahydrofuran (70 ml) is added during 15 min. The reaction mixture is then poured into a solution of sodium cyanide (40 g) and ammonium chloride (59 g) in water (400 ml) and kept 1 hour at room temperature. After saturation with sodium chloride, the tetrahydrofuran layer is separated and evaporated under reduced pressure. The residue is dissolved in diethyl ether, washed with water, dried with sodium sulfate and evaporated to give crude 2-fluoromethyl-2-amino-3-pentenenitrile (1:1 cis/trans mixture, 21.5 g) as a dark coloured oil which is used for the next step without further purification.

NMR (CDCl$_3$) δ:

cis: *)1.97 (3H, d of narrow d, J=7 Hz, J$_{allyl}$≃2 Hz); 2.20 (—NH$_2$, broad s), 4.32 (2H, d of AB, J$_{AB}$=8.5 Hz, J$_{H-F}$=46 Hz), 5.12 (1H, center of A part of ABX$_3$, J$_{AB}$=12 Hz, additional allylic coupling), 5.82 (1H, center of B part of ABX$_3$, 2q, J$_{AB}$=12 Hz, J$_{BX}$=7 Hz).

trans: *)1.77 (3H, d of narrow d, J=7 Hz, J$_{allyl}$≃1 Hz), 2.20 (—NH$_2$, broad s), 4.25 (2H, d, J$_{HF}$=46 Hz), 5.27 (1H, center of A part of ABX$_3$, J$_{AB}$=15 Hz, additional allylic coupling), 6.13 (1H, center of B part of ABX$_3$, 2q, J$_{AB}$=15 Hz, J$_{BX}$=7 Hz).

*Assignment of signals is possible by partial separation of the isomers by liquid-liquid partition (water/diethyl ether).

B. 2-Fluoromethyl-2-trifluoroacetamido-3-pentenenitrile

2-Fluoromethyl-2-amino-3-pentenenitrile (21.5 g, 168 mmol) prepared as in Step A above dissolved in methylene chloride (300 ml) is cooled to −30° C. and treated with trifluoroacetic anhydride (34.8 g, 1.66 mmol). The mixture is allowed to warm up to room temperature overnight and the solvent is removed under reduced pressure. Dissolving the residue in ethyl acetate, washing with water, drying with sodium sulfate and evaporation gives a dark oil (35 g). TLC (ethyl acetate/petroleum ether 40:60) indicates two major spots with Rf 0.65 and 0.60 corresponding respectively to the cis and trans isomers of 2-fluoromethyl-2-trifluoroacetamido-3-pentenenitrile.

Rapid chromatography and collection of the fractions corresponding to these Rf values gave 2-fluoromethyl-2-trifluoroacetamido-3-pentene-nitrile (1:1 cis/trans mixture, 23.5 g) as a slightly yellow oil.

NMR (CDCl$_3$) δ:

cis: **1.93 (3H, d, J=7 Hz, small allylic coupling), 4.68 (2H, d, J$_{H-F}$=46 Hz), 5.37 (1H, center of A part of ABX$_3$, J$_{AB}$=12 Hz, additional allylic coupling), 6.00 (1H, center of B part of ABX$_3$, 2q, J$_{AB}$=12 Hz, J$_{BX}$=7 Hz), 7.6 (NH, broad s).

trans: **1.82 (3H, d, J=7 Hz, small allylic coupling), 4.62 (2H, d, J$_{H-F}$=46 Hz), 5.40 (1H, center of A part of ABX$_3$, J$_{AB}$=15 Hz, additional allylic coupling), 6.27 (1H, center of B part of ABX$_3$, 2q, J$_{AB}$=15 Hz, J$_{BX}$=7 Hz), 7.6 (NH, broad s).

**A small amount of cis/trans mixture is partially separated into the isomers by chromatography.

C. 2-Fluoromethyl-2-trifluoroacetamido-5-bromo-3-(E)-pentenenitrile

A mixture of 2-fluoromethyl-2-trifluoroacetamido-3-pentenenitrile, (23.5 g, 105 mmol) prepared as in Step B above, N-bromosuccinimide (19 g, 108 mmol), carbon tetrachloride (160 ml), and benzoylperoxide is irradiated and heated under reflux by means of a 325 W lamp for 30 min. During this time, succinimide separates together with an oil which are both collected by filtration on a fritted glass. Dissolving in chloroform, removal of succinimide by filtration and evaporation gives crude 2-fluoromethyl-2-trifluoroacetamido-5-bromo-3-(E)-pentenenitrile (31 g) as a brown oil, which is used for the next step without further purification.

NMR (CDCl$_3$) δ: 2.75 (succinimide), 3.97 (2H, d, J=7 Hz), 4.68 (2H, d, J$_{H-F}$=46 Hz), 5.73 (1H, center of A part of ABX$_2$, J$_{AB}$=15 Hz), 6.43 (1H, center of B part of ABX$_2$, 2t, J$_{AB}$=15 Hz, J$_{BX}$=7 Hz), 7.75 (NH, broad s).

D. 2-Fluoromethyl-2-trifluoroacetamido-5-hexamethylene tetrammonium-3-(E)-pentenenitrile bromide To a solution of 2-fluoromethyl-2-trifluoroacetamido-5-bromo-3-(E)-pentenenitrile (15.0 g, 49.5 mmol) prepared as in Step C above in chloroform (40 ml) is added hexamethylenetetramine (6.93 g, 49.5 mmol) in 80 ml of chloroform. A brown oil separates which solidifies on standing overnight. The crude product (14.7 g) is recrystallized by dissolving in hot methanol and addition of twice the volume of chloroform to give pure 2-fluoromethyl-2-trifluoroacetamido-5-hexamethylenetetrammonium-3-(E)-pentenenitrile bromide (11.3 g) as heavy colourless crystals containing 1 mole of chloroform, mp 147° C.

Analysis for C$_{15}$H$_{20}$BrCl$_3$F$_4$N$_6$O: Calculated: C, 32.02; H, 3.58; N, 14.94%. Found: C, 32.00; H, 3.51; N, 15.30%.

NMR (CD$_3$OD) δ: 3.50 (2H, broad d, J=6–7 Hz), 4.43 (6H, s), 4.63 (2H, d, J$_{H-F}$=76 Hz), 4.95 (6H, s), 6.07 (2H, m), 7.58 (1H, CHCl$_3$, s)

E. 2-Fluoromethyl-2,5-diamino-3-(E)-penten-1-oic acid

2-Fluoromethyl-2-trifluoroacetamido-5-hexamethylenetetrammonium-3-(E)-pentenenitrile bromide (5.62 g, 10 mmol) prepared as in Step D above is dissolved in conc. hydrochloric acid (100 ml) and evaporated to dryness at 35° C. under reduced pressure. This operation is repeated twice more. The residue is heated with conc. hydrochloric acid (100 ml) at 100° C. overnight (16 hours) whilst a slow stream of nitrogen is passed through the solution. After evaporating the dark coloured reaction mixture under reduced pressure and drying for several hours with an oil pump, the residue is dissolved in dry ethanol (50 ml), ammonium chloride is removed by filtration and propylene oxide (1.8 g) is added to precipitate the crude monohydrochloride. After standing at 5° C. overnight, a brown, hygroscopic precipitate is collected on a fritted glass, washed with a small amount of dry ethanol, dissolved in water and treated with charcoal at 40°–50° C. for 2 hours. Evaporation of the colourless filtrate gives a white solid which is recrystallized to give pure 2-fluoromethyl-2,5-diamino-3-(E)-penten-1-oic acid, monohydrochloride (730 mg) as colourless crystals, mp 176° C. (dec).

NMR ($D_2O$/DCl) δ: 3.83 (2H, broad d), 4.87 (1H, center of A part of ABX, $J_{AB}=11$ Hz, $J_{AX}=J_{H-F}=47$ Hz), 5.23 (1H, center of B part of ABX, $J_{AB}=11$ Hz, $J_{BX}=J_{H-F}=45$ Hz), 6.18 (2H, m).

Analysis for $C_6H_{12}ClFN_2O_2$: Calculated: C, 36.28; H, 6.09; N, 14.10%. Found: C, 36.10; H, 5.88; N, 13.85%.

EXAMPLE 2

5-Fluoromethyl-2,5-diaminovaleric acid
(α-Fluoromethyl-ornithine)

A. 2-Fluoromethyl-2-amino-5-methoxy-valeronitrile

Under an atmosphere of nitrogen, 3-methoxypropyl magnesium chloride is prepared from 3-methoxy-1-chloropropane (5.43 g, 50 mmol, prepared according to Haworth and Perkin, Chem. Zentralblatt II 1271 (1912) and magnesium turnings (1.22 g, 50 mmol) in dry THF (50 ml). The mixture is heated under reflux for 3 hours, then cooled to −30° C. and a solution of fluoroacetonitrile (2.95 g, 50 mmol) in THF (30 ml) is added during 20 minutes. After keeping the mixture at −30° C. for ½ hour more, a solution of sodium cyanide (4.9 g, 100 mmol) and ammonium chloride (8.09 g, 150 mmol) in water (100 mL), previously cooled to 0° C., is added and the mixture is stirred for ¾ hours at room temperature. After saturating with sodium chloride, the THF layer is separated and the aqueous phase is extracted twice with ether. After drying ($Na_2SO_4$), the combined organic extracts are evaporated to give 2-fluoromethyl-2-amino-5-methoxyvaleronitrile (4.0 g) as a brown oil.

NMR ($CDCl_3$) δ: 1.77 (4H, m), 2.10 (broad s, $NH_2$), 3.30 (3H, s), 3.40 (2H, t), 4.32 (2H, ABX, $J_{AB}=9$ Hz, $J_{AX}=J_{BX}=J_{H-F}=47$ Hz).

B.
2-Fluoromethyl-2-phthalimido-5-methoxy-valeronitrile

To a solution of 2-fluoromethyl-2-amino-5-methoxy-valeronitrile (1.62 g, 10 mmol) and triethylamine (2.02 g, 20 mmol) in methylene chloride (30 ml), cooled to −20° C., is added phthaloyldichloride (2.03 g, 10 mmol) in methylene chloride (10 mL). The mixture is allowed to warm up to room temperature overnight. After washing with water, 1 N HCl, water again, and drying ($Na_2SO_4$), the solvent is removed under reduced pressure to give 2.4 g of crude material. This is purified by chromatography on silica (ethyl acetate/petroleum ether 3:7).

NMR ($CDCl_3$): δ 2.15 (4H, m), 3.23 (3H, s), 3.40 (2H, t, J=6 Hz), 5.02 (2H, ABX, $J_{AB}=9$ Hz, $J_{AX}=J_{BX}=J_{H-F}=46$ Hz), 7.77 (4H, s).

C. 2-Fluoromethyl-2-phthalimido-5-iodo-valeronitrile

2-Fluoromethyl-2-phthalimido-5-methoxy-valeronitrile (1.20 g, 4.14 mmol), trimethylsilyl iodide (3.2 g, 16 mmol) and chloroform (15 ml) are heated to 60° C. under nitrogen for 48 hours. After removal of the solvent, the residue is dissolved in chloroform, washed with water, sodium thiosulfate solution and water again, dried and evaporated to give the crude product as an oil (1.2 g). This is purified by chromatography on silica (ethyl acetate/petroleum ether 1:3) to give pure 2-fluoromethyl-2-phthalimido-5-iodo-valeronitrile.

NMR ($CDCl_3$) δ: 2.0 (4H, m), 3.10 (2H, t), 4.90 (2H, ABX, $J_{AB}=9$ Hz, $J_{AX}=J_{BX}=J_{H-F}=46$ Hz), 7.70 (4H, s).

D. 2-Fluoromethyl-2,5-diphthalimido-valeronitrile

2-Fluoromethyl-2-phthalimido-5-iodo-valeronitrile (1.20 g, 3.11 mmol) and potassium phthalimide (0.75 g, 4 mmol) are heated in dimethylformamide (25 ml) to 80° C. for 2 hours. After standing overnight at room temperature, the DMF is removed by vacuum distillation and the residue is dissolved in chloroform and washed with 1 N KOH and water. After drying ($Na_2SO_4$), evaporation gives 2-fluoromethyl-2,5-diphthalimidovaleronitrile as a solid.

NMR ($CDCl_3$) δ: 2.17 (4H, m), 3.73 (2H, t), 4.93 (2H, ABX, $J_{AB}=9$ Hz, $J_{AX}=J_{BX}=J_{H-F}=46$ Hz), 7.73 (8H, broadened s).

E. 2-Fluoromethyl-2,5-diaminovaleric acid

2-Fluoromethyl-2,5-diphthalimido valeronitrile (1.21 g, 3 mmol) is refluxed with conc. hydrochloric acid (20 ml) for 4 days. After standing at room temperature for several hours, phthalic acid is removed by filtration, the filtrate is evaporated, the residue dissolved in 2 N HCl (20 ml) and carefully extracted with ether (5×10 ml). After evaporation, the residue is dried carefully under vacuum (oil pump) overnight. It is dissolved in dry ethanol (7 ml) and, after filtration, propylene oxide (0.3 g, 5 mmol) in ethanol (1 ml) is added to precipitate the monohydrochloride. This is collected after standing overnight at room temperature and recrystallized from water/ethanol to give pure 2-fluoromethyl-2,5-diaminovaleric acid, monohydrochloride, mp 260° C. (dec); TLC (EtOH/$NH_4OH$ 80/20): 0.18.

NMR ($D_2O$) δ: 1.93 (4H, m), 3.10 (2H, broad t), 4.83 (2H, ABX, $J_{AB}=10$ Hz, $J_{AX}=J_{BX}=J_{H-F}=46$ Hz).

EXAMPLE 3

2-Amino-2-fluoromethyl-3-(2,3-dihydroxyphenyl)propionic acid

A. 2,3-Dimethoxybenzyl chloride

Thionyl chloride (288 g) is added over 1.5 hour to a stirred solution of 2,3-dimethoxybenzyl alcohol (400 g) and 2,6-lutidine in methylene chloride (2 l). The reaction mixture is then stirred for 30 minutes after which it is washed with 2 N hydrochloric acid (7×1 l) and then with water. The organic layer is separated, dried ($MgSO_4$) and evaporated to give a residue, which upon distillation yields 3,4-dimethoxybenzyl chloride (375 g), b.p. 145°–150° C. at 20–25 nm (water-pump vacuum). The material solidifies on standing.

B.
2-Amino-2-fluoromethyl-3-(2,3-dimethoxyphenyl)propionitrile

Ethyl bromide (1 ml) is added to magnesium turnings (48 g) and magnesium powder (48 g) covered with tetrahydrofuran (THF) (800 ml). 2,3-Dimethoxybenzyl chloride (336 g) in THF (2000 ml) is then added over 2.5 hours while the reaction mixture is maintained at 20° C. by means of a water bath. After the addition, the mixture is stirred for one additional hour and excess magnesium is removed by decantation. The Grignard reagent thus obtained is cooled to −35° C. and fluoroacetonitrile (105 g) in THF (600 ml) is added at −40° C. to −30° C. Cooling is continued for one hour. The reaction mixture is poured into a solution of sodium cyanide (175 g) and ammonium chloride (275 g) in water (4 l) at 10° C. After the mixture is stirred for 30 minutes, the organic phase is separated. The water phase is saturated with sodium chloride (250 g) and is washed with ether (3×1 l). The combined organic phases are dried (MgSO$_4$), filtered, and evaporated to dryness. The residue, dissolved in ether (2 l), is extracted with 10% hydrochloric acid (4×250 ml) and the acid phases are combined, extracted with diethyl ether, and made basic with conc. ammonium hydroxide. The oil, which separates, is taken up into diethyl water (1 l), and the solution is dried (MgSO$_4$), filtered, and evaporated to give the propionitrile product (110 g) as a brown oil.

C.
2-Amino-2-fluoromethyl-3-(2,3-dihydroxyphenyl)propionic acid

2-Amino-2-fluoromethyl-2-(2,3-dimethoxyphenyl)-propionitrile (100 g) and 48% hydrobromic acid (500 ml) are heated under reflux overnight. The hot solution is treated with charcoal (5 g), filtered, and evaporated to dryness over water-pump vacuum. The residue is treated with water (250 ml) and the mixture taken to dryness. This procedure is repeated. The residue is taken up in hot isopropanol (500 ml). After filtration of the insoluble ammonium bromide, the solution is concentrated (to about 400 ml). Trimethylamine is then added to adjust the pH to 5, and diethylether (1 l) is added. A solid which separates is collected and washed with chloroform 4×250 ml). The remaining solid is dried and taken up in boiling water (1 l). Charcoal is added. After removal of the charcoal by filtration, the mixture is concentrated (to about 400 ml) and cooled. The light brown solid which separates is collected and washed with cold isopropanol and diethylether. Recrystallization three times from water, gives the title product (24 g), m.p. 224° C. (dec).

EXAMPLE 4
2-Amino-2-fluoromethyl-3-(2,5-dihydroxyphenyl)propionic acid

A. Fluoroacetonitrile

A stirred mixture of phosphorus pentoxide (200 g), fluoroacetamide (150 g) and hexamethylphosphoramide (500 ml), in a 2 l reactor fitted with a simple distillation head, a distillation condenser and a receiver cooled in a mixture of solid carbon dioxide/acetone, is slowly heated to 50° C. under a pressure of 90 mm Hg. At this temperature a vigorous reaction commences and fluoroacetonitrile begins to distil at 38° C.

After the vigorous reaction has subsided (~3 minutes) the temperature of the oil bath is slowly raised to 140° C. and the remaining fluoroacetonitrile is collected at 38°–50° C. The fluoroacetonitrile (111 g) is obtained as a colorless liquid. An NMR analysis shows that it contains traces of hexamethyl phosphoramide which can be removed, if desired, by a redistillation, but its presence is not detrimental for the subsequent Grignard reaction.

B. 2,5-Dimethoxybenzyl chloride

Thionyl chloride (108 g) is slowly added during 1 hour to a stirred mixture of 2,5-dimethoxybenzyl alcohol (150 g), 2,4,6-collidine (108 g), and methylene chloride (750 ml) at room temperature. The reaction is slightly exothermic. After stirring for another 30 minutes, the mixture is washed with hydrochloric acid (2 N) and water and then dried (MgSO$_4$). Evaporation gives a residue of 2,5-dimethoxybenzyl chloride which crystallizes (127 g).

Analysis for C$_9$H$_{11}$Cl: Calculated: C, 57.92; H, 5.94%. Found: C, 57.93; H, 5.94%.

C.
2-Amino-2-fluoromethyl-3(2,5-dimethoxyphenyl)propionitrile

Ethyl bromide (2 ml) is added to magnesium turnings (25 g, 1 mol) covered with anhydrous tetrahydrofuran at room temperature under nitrogen. When the reaction has subsided, 2,5-dimethoxybenzyl chloride (102.5 g, 0.55 mol) in anhydrous tetrahydrofuran (200 ml) is slowly added at such a rate to cause a gentle reflux. After stirring for a further hour, the Grignard solution is decanted from the excess magnesium (11.7 g), cooled to −35° C., and treated with a solution of fluoroacetonitrile (33.6 g, 0.59 mol) in anhydrous tetrahydrofuran (200 ml) by dropwise addition, a nitrogen atmosphere being maintained throughout. The mixture is stirred for a further hour at −35° C. and then poured into a stirred solution of sodium cyanide (55 g) and ammonium chloride (88 g) in water (1 l) at 10° C. The mixture is stirred for 30 minutes. The organic phase is then separated. The aqueous phase is saturated with sodium chloride and extracted with ether (2×). The combined organic phases are charcoaled, dried (MgSO$_4$), filtered, and evaporated to give an oil (112 g). A solution of the oil in anhydrous diethylether is treated with ethereal hydrogen chloride and the precipitated oil is crystallized by trituration. The solid is filtered and washed well with ether to give crude 2-amino-2-fluoromethyl-3(2,5-dimethoxyphenyl)propionitrile as the hydrochloride (80 g).

D.
2-Amino-2-fluoromethyl-3(2,5-dimethoxyphenyl)propionamide

The amino nitrile prepared in Step C (80 g) is dissolved in the minimum of methanol and treated with an equal volume of methanol saturated with hydrogen chloride at 0° C. The mixture is allowed to stand in a refrigerator overnight and then evaporated. The residue is crystallized by trituration under ether to give 2-amino-2-fluoromethyl-3(2,5-dimethoxyphenyl)propionamide as the hydrochloride (68 g).

E.
2-Amino-2-fluoromethyl-3(2,5-dihydroxyphenyl)propionic acid

A mixture of the amide prepared in Step D (68 g) in 47% hydrobromic acid (250 ml) is refluxed for 1 night under nitrogen. The hot solution is treated with charcoal, filtered, and evaporated to dryness. Dioxane is added to the residue and evaporated to remove the last traces of water. Dioxane treatment is repeated once. A solution of the residue in isopropanol is filtered to remove ammonium bromide and concentrated to about 250 ml. The pH of the solution is adjusted to 5 by the addition of triethylamine in isopropanol to begin crystallization. Anhydrous ether (~1 l) is added, the mixture is filtered, and the solid so obtained is washed with chloroform to remove triethylamine hydrobromide.

The solid is dissolved in water (1 l at 100°) and the solution is charcoaled and evaporated to about 500 ml to give crystals of 2-amino-2-fluoromethyl-3-(2,5-dihydroxyphenyl)propionic acid as the dihydrate (21 g). A further 10 g is obtained by concentration of the mother liquors, m.p. 212° C.

EXAMPLE 5

2-Amino-2-fluoromethyl-3-(2-hydroxy-3-methylphenyl)propionic acid

A.

2-Amino-2-fluoromethyl-3-(2-methoxy-3-methyl)phenyl propionitrile

All manipulations are carried out in an atmosphere of nitrogen.

A solution of ethylene dichloride (10.59 g, 0.107 mol) in anhydrous tetrahydrofuran (THF) (150 ml) is slowly added to a stirred mixture of magnesium turnings (2.59, 0.107 mol) and anhydrous THF (50 ml). The vigorous exothermic reaction is controlled by cooling with ice-cold water. The reaction is finally warmed at 30° C. to dissolve all the magnesium and the solution so obtained is added to a freshly prepared solution of sodium (4.9 g, 0.214 mol) in a mixture of naphthalene (28.2 g, 0.22 mol) and anhydrous tetrahydrofuran (200 ml). An intermediate fine black suspension of magnesium is formed.

Magnesium turnings (2.5 g, 0.107 mol) are added to the above suspension to maintain an excess of magnesium, and the stirred mixture cooled to −20° C. A solution of 2-methoxy-3-methylbenzyl chloride (18.3 g, 0.107 mol) in THF (50 ml) is added during an hour, the black color of the mixture disappearing at the end of the addition. The solution is decanted from the excess magnesium and treated with a solution of fluoroacetonitrile (6.3 g, 0.107 mol) in anhydrous tetrahydrofuran (50 ml) at −20° C. by dropwise addition during 30 minutes. The mixture is stirred for a further hour at −20° C. and poured into a stirred aqueous solution of a mixture of sodium cyanide (10.49 g, 0.214 mol) and ammonium chloride (17.2 g, 0.32 mol).

After half an hour, the organic layer is separated using diethyl ether, dried, and concentrated to ⅓ volume. Ethereal hydrogen chloride is added and the mixture is allowed to crystallize. The crystals of 2-amino-2-fluoromethyl-3-(2-methoxy-3-methylphenyl)propionitrile, hydrochloride (m.p. 128° C.) are filtered off and recrystallized from acetonitrile (8 g).

B.

2-Amino-2-fluoromethyl-3-(2-methoxy-3-methylphenyl)propionamide

A solution of 2-amino-2-fluoromethyl-3-(2-methoxy-3-methylphenyl)propionitrile hydrochloride (5.2 g) in methanol saturated with hydrogen chloride (100 ml) is allowed to stand for 64 hours in a refrigerator. The methanol is evaporated, the residue is dissolved in water, and the solution basified by the addition of aqueous potassium carbonate. The organic material (4.8 g) is isolated by extraction with dichloromethane. The syrup is purified first by column chromatography using silica and a mixture of chloroform 93% and acetone 7% eluant, and finally by crystallization from benzene to give crystals of 2-amino-2-fluoromethyl-3(2-methoxy-3-methylphenyl)propionamide, m.p. 118° C. (3.5 g).

C.

2-Amino-2-fluoromethyl-3-(3-hydroxy-3-methylphenyl)propionic acid

A solution of 2-amino-2-fluoromethyl-3-(2-methoxy-3-methylphenyl)propionamide (1.5 g) in 48% hydrobromic acid is refluxed overnight, the acid evaporated, and the residue dissolved in isopropanol. After removing the ammonium bromide by filtration, the pH of the solution is adjusted to 5 by the addition of triethylamine. The crystals which separate are filtered, washed well with chloroform, and dissolved in water. The aqueous solution is evaporated and the residue crystallized from ethanol to give 2-amino-2-fluoromethyl-3-(2-hydroxy-3-methylphenyl)propionic acid, as the semi-hydrate, m.p. 168° C.

EXAMPLE 6

2-Amino-2-fluoromethyl-3-(3-hydroxy-4-methoxyphenyl)propionic acid

A.

2-Amino-2-fluoromethyl-3-(3-benzyloxy-4-methoxyphenyl)propionitrile

Under an atmosphere of nitrogen, 3-benzyloxy-4-methoxybenzyl magnesium chloride is prepared from 3-benzyloxy-4-methoxybenzylchloride (C. Schöpf and L. Winterhalder, Ann. 544, 62 (1940) (22.0 ng, 84 mmol) and magnesium turnings (4.1 g) in tetrahydrofuran (THF) (100 ml) at room temperature (about 2 hours). After cooling to −30° C., a solution of fluoroacetonitrile (4.94 g) in THF (40 ml) is added dropwise, maintaining the temperature between −30° C. and −40° C. Stirring is continued at this temperature for another 30 minutes, then the mixture is poured into a solution of sodium cyanide (12.3 g) and ammonium chloride (17.9 g) in water (150 ml), previously cooled with ice. After stirring for 30 minutes, the mixture is saturated with sodium chloride whereupon the phases separate. After extracting the aqueous phase two more times with diethyl ether, the combined THF and ether phases are dried ($Na_2SO_4$) and evaporated to give the crude aminonitrile (25.9 g) as a brown oil. The oil is dissolved in ether and treated with HCl gas to prepare the hydrochloride as an oil. This oil is recrystallized twice from ethanol/ether to give 2-fluoromethyl-2-amino-3-(3'-benzyloxy-4'-methoxyphenyl)propionitrile as the hydrochloride as a slightly colored solid;

NMR ($CD_3OC$): 3.47 ppm (3H, s), 4.32 ppm (2H, d, $J_{H-F}$=46 Hz), 4.73 ppm (2H, s), 6.60 ppm (3H, m), 6.97 ppm (5H, m).

B.

2-Amino-2-fluoromethyl-3-(3-hydroxy-4-methoxyphenyl)propionic acid

A solution of 2-amino-2-fluoromethyl-3-(3-benzyloxy-4-methoxyphenyl)propionitrile (0.7 g) in absolute methanol saturated with dry hydrogen chloride (50 ml) is heated at reflux for 12 hours. The methanol is evaporated and the residue dissolved in trifluoroacetate acid (10 ml). The mixture is heated at reflux temperature for 2 hours. Water (4 ml) is then added, and reflux continues overnight. The residue obtained upon evaporation under reduced pressure is passed through Amberlite 120 H+ ion exchange resin column. The fractions are pooled and concentrated. The residue is crystallized from water-methanol-ether to afford the desired product.

EXAMPLE 7

Methyl 2-amino-2-fluoromethyl-3-(4-hydroxyphenyl)propionate

A.
2-Amino-2-fluoromethyl-3-(4-methoxyphenyl)propionitrile

Under nitrogen, 4-methoxybenzylmagnesium chloride is prepared by adding 4-methoxybenzyl chloride (160 g) in tetrahydrofuran (THF) (800 ml) to magnesium turnings (50 g) and THF (400 ml) within about 2 hours. The reaction is initiated by the addition of a few drops of methyl iodide, and the reaction flask is cooled by a bath containing water of room temperature. Stirring is continued for an additional ½ hour, and the solution is decanted from the excess of magnesium, transferred to a second flask and cooled to $-30°$ C. to $-40°$ C. Fluoroacetonitrile (58 g) in THF (250 ml) is added dropwise within 40 minutes, keeping the temperature (internal) between $-30°$ C. and $-40°$ C. After the addition, stirring is continued for 10 minutes at the same temperature then the reaction mixture is poured into a stirred solution of sodium cyanide (100 g) and ammonium chloride (100 g) in water (2 l) and stirred for 1 hour at room temperature. Sodium chloride (400 g) is added to separate the phases. The THF layer (upper phase) is removed, and the aqueous layer is extracted with diethyl ether ($3 \times 1$ l). After drying ($Na_2SO_4$) the THF solution and the ethereal extracts are stripped to give 200 g of crude product. Treatment of a solution of the crude nitrile in diethyl ether (3 l) with HCl gas precipitates the hydrochloride which is recrystallized from ethanol/ether (120 g).

B.
2-Amino-2-fluoromethyl-3-(4-hydroxyphenyl)propionic acid

Under nitrogen, 2-amino-2-fluoromethyl-3-(4-methoxyphenyl)propionitrile, hydrochloride (30 g) and conc. hydrobromic acid (500 l) are heated at 90° C. for 30 hours. After evaporation, the residue is dissolved in water, and aqueous ammonia is added until pH 5.5. The precipitate is collected, dried and washed several times carefully with acetone. The washed precipitate is dissolved in 2 N hydrochloric acid, treated with charcoal, and reprecipitated by addition of ammonia (pH 5.5). Reprecipitation in the same manner gives 2-amino-2-fluoromethyl-3-(4-hydroxyphenyl)propionic acid (16.6 g), m.p. 239° C. (dec.).

Analysis for $C_{10}H_{12}FNO_3$: Calculated: C, 56.33; H, 5.67; N, 6.57%. Found: C, 56.34; H, 5.73; N, 6.42%.

C. Methyl 2-amino-2-fluoromethyl-3-(4-hydroxyphenyl)propionate

With ice cooling, a suspension of 2-amino-2-fluoromethyl-3-(4-hydroxyphenyl)propionic acid (10.0 g) in absolute methanol (400 ml, dried over magnesium) is saturated with HCl gas. After heating at 90° C. overnight, the solvent is removed under reduced pressure, and the residue is dried for 3 hours under the vacuum of an oil pump. After dissolving in absolute methanol (400 ml) and saturating with HCl gas, the mixture is heated at 90° C. overnight again. After evaporation of the solvent, the residue is dissolved in water and a solution of sodium carbonate is added with stirring until pH ~10. The suspension is extracted 3 times with ether; the combined ether extracts are filtered, washed carefully with water, dried ($Na_2SO_4$) and evaporated to give pure methyl-2-amino-2-fluoromethyl-3-(4-hydroxyphenyl)-propionate (7.5 g, 70%) as white crystals, m.p. 130° C.

Analysis for $C_{11}H_{14}FNO_3$: Calculated: C, 58.14; H, 6.21; N, 6.16%. Found: C, 58.32; H, 6.34; N, 6.18%.

NMR (CD$_3$OD) δ: 2.77 (2H, AB, $J_{AB}=14$ Hz), 3.70 (3H, s), 4.50 (2H, ABX, $J_{AB}=9$ Hz, $J_{AX}=J_{BX}J_{H-F}=46$ Hz), 6.87 (4H, $A_2B_2$ with additional fine splitting, $J_{AB}=9$ Hz).

EXAMPLE 8

2-Fluoromethyl-2,5-diaminovaleric acid (α-Fluoromethylornithine)

A. 1-Chloro-3-benzyloxypropane

In a 2 l flask, a mixture of 3-chloropropanol (56.7 g), benzyl bromide (102.6 g) and dry THF (600 ml) is stirred and cooled with ice/salt mixture. Potassium tert-butoxide (70 g) is added in portions (5–10 g), maintaining the internal temperature at about 0° C. After the mixture is stirred for 3 more hours at room temperature, the solvent is evaporated. Addition of 1 N HCl (1 l), extraction with ether (1 l), and evaporation of solvent gives crude material (113.6 g), which is distilled under vacuum to give the title compound, (108.4 g), $bp_{0.01}$ 60°–80° C.

NMR (CDCl$_3$) δ: 1.97 (2H, q, J=6 Hz), 3.50 and 3.55 (4H, 2t, J=7 Hz), 4.41 (2H, s), 7.24 (5H, s).

B. 2-Fluoromethyl-2-amino-5-benzyloxyvaleronitrile

To magnesium turnings (30.6 g, 1.26 mol), suspended in dry ether (150 ml) is added methyl iodide (≈0.5 ml) and then a solution of 1-chloro-3-benzyloxypropane (116 g, 0.63 mol) in ether (1.1 l) at such a rate that gentle reflux is maintained. (This procedure is performed under nitrogen). After the mixture is heated for 1 more hour under reflux, titration indicates Grignard formation to be complete. The solution is separated from the excess of magnesium (glass wool), transfered to a 6 l flask and, again under nitrogen, cooled to $-40°$ C. Fluoroacetonitrile (33.48 g, 0.57 mol) in ether (300 ml) is added slowly. The mixture is then kept at $-40°$ C. for another ½ hour and is poured into a mixture of sodium cyanide (123 g), ammonium chloride (186 g), ice (600 g), and water (650 ml). The mixture is stirred vigorously and allowed to warm up to room temperature during 1 hour. Ether is added, the aqueous phase is saturated with sodium chloride, and the organic layer is separated. The aminonitrile is extracted with 1 N HCl ($2 \times 750$ ml) and re-extracted with ether ($2 \times 750$ ml) after basification with concentrated ammonia. Drying ($Na_2SO_4$) and evaporation gives the title compound as a brown oil (74.8 g).

NMR (CDCl$_3$) δ: 1.38–2.43 (4H, m), 3.45 (2H, m), 4.28 (2H, ABX, $J_{AB}=9$ Hz, $J_{AX}=J_{BX}=J_{H-F}=47$ Hz), 4.47 (2H, s), 7.30 (5H, s).

The product can be used for the next step without further purification.

C. 2-Fluoromethyl-2-phthalimido-5-benzyloxy-valeronitrile

To a stirred mixture of 2-fluoromethyl-2-amino-5-benzyloxy-valeronitrile (74.8 g), triethylamine (100 g), and dry dichloromethane (450 ml), cooled in an ice bath, a solution of phthaloyldichloride (58 g) in dichloromethane (300 ml) is added slowly. Stirring is continued at room temperature overnight. The mixture is extracted with 2 N HCl (2×750 ml), washed with water (2×750 ml), dried carefully (Na₂SO₄), and evaporated to give a brown oil which, according to NMR analysis, contains some iso-phthalimide. The oil is dissolved in dry dichloromethane (500 ml), triethylamine (100 g) is added, and the mixture is refluxed for 3 hours. Work-up as described above gives an oil which is purified by flash-chromatography on silica (2 kg, petroleum ether-/ethyl acetate 4:1). Crystallisation from ether gives the title compound (49.4 g).

NMR (CDCl₃) δ: 1.5–3.0 (4H, m), 3.52 (2H, t), 4.44 (2H, s), 5.03 (2H, ABX, $J_{AB}$=90 Hz, $J_{AX}=J_{BX}=J_{H-F}$=47 Hz), 7.30 (5H, s), 7.80 (4H, s).

D. 2-Fluoromethyl-2-phthalimido-5-hydroxy-valeronitrile

To a solution of 2-fluoromethyl-2-phthalimido-5-benzyloxy-valeronitrile (49.4 g) in dry dichloromethane (400 ml) is added TMSI (45 ml, 2.2 equivalents), and the mixture is stirred at room temperature overnight. The solvent is removed under vacuum. The residue is evaporated two times more with dichloromethane and then dissolved in chloroform. After addition of triethylamine (60 ml), the mixture is refluxed for 3 hours. Washing with water, 1 N HCl (2×), water again, drying, and evaporation gives the title compound as a brown oil (42.8 g).

NMR (CDCl₃) δ: 1.0–2.9 (6H+OH, m), 3.65 (2H, t+additional splitting), 5.03 (2H, ABX, $J_{AB}$=9 Hz, $J_{AX}=J_{BX}=J_{H-F}$=47 Hz), 7.80 (4H, s).

E. 2-Fluoromethyl-2-phthalimido-5-methane-sulfonyloxy-valeronitrile

A mixture of 2-fluoromethyl-2-phthalimido-5-hydroxy-valeronitrile (42.8 g), dry pyridine (170 ml), and dry dichloromethane (350 ml) is stirred and cooled with ice/salt mixture. Freshly distilled methanesulfonylchloride (15.7 g) in dichloromethane (200 ml) is slowly added, and stirring is continued at room temperature overnight. The mixture is then poured onto ice/2 N HCl, and the organic phase is extracted subsequently with 1 N HCl, water, 10% sodium bicarbonate, and water (3×). Drying (MgSO₄), treatment with charcoal (room temperature), and evaporation gives the title compound as a brown oil (42 g).

NMR (CDCl₃) δ: 1.1–2.9 (4H, m), 3.03 (3H, s), 4.31 (2H, t+additional splitting), 5.03 (2H, ABX, $J_{AB}$=9 Hz, $J_{AX}=J_{BX}=J_{H-F}$=47 Hz), 7.86 (4H, s).

F. 2-Fluoromethyl-2-phthalimido-5-iodo-valeronitrile

A solution of 2-fluoromethyl-2-phthalimido-5-methanesulfonyloxy-valeronitrile (42 g) and sodium iodide (35.7 g) in acetone (600 ml) is stirred and heated under reflux. After about ½ hour, the mixture solidifies. Acetone (500 ml) is added, and refluxing and stirring is continued overnight. The salts are removed by filtration and washed several times with acetone. The acetone is evaporated to give a residue which is dissolved in ether (1.5 l). The ether solution is washed subsequently with water (2×), sodium sulfite solution, and water again (3×). After drying (MgSO₄) and evaporating the ether, the title compound is obtained as an oil (34.1 g).

NMR (CDCl₃), δ: 1.0–2.9 (4H, m), 3.16 (2H, t), 4.97 (2H, ABX, $J_{AB}$=9 Hz, $J_{AX}=J_{BX}=J_{H-F}$=47 Hz), 7.80 (4H, s).

G. 2-Fluoromethyl-2,5-diphthalimido-valeronitrile

A mixture of 2-fluoromethyl-2-phthalimido-5-iodo-valeronitrile (34.1 g), potassium phthalimide (16.6 g), and dry DMF (230 ml) is stirred and heated at 70°–80° C. for 5 hours. The DMF is removed under reduced pressure, the residue is dissolved in chloroform, and the chloroform solution is washed with water (2×), 1 N KOH (2×), 1 N HCl, and water again (3×). The washed chloroform solution is dried and solvent removed to give an oil which is evaporated twice with chloroform/ether to give a solid. Recrystallization from ether (500 ml) gives the pure title compound (18.5 g).

NMR (CDCl₃) δ: 1.5–2.9 (4H, m), 3.78 (2H, t), 5.03 (2H, ABX, $J_{AB}$=9 Hz, $J_{AX}=J_{BX}=J_{H-F}$=47 Hz), 7.76 (8H, s).

H. 2-Fluoromethyl-2,5-diphthalimido-valeronitrile (18.5 g) is heated under reflux with concentrated HCl for 4 days. After the reaction mixture is cooled to room temperature, phthalic acid is removed by filtration, and the filtrate is evaporated to dryness. The residue is dissolved in water, and the water solution is extracted twice with ether and then taken to dryness. Last traces of water and HCl are removed by evaporating the residue twice with isopropanol. The residue is dissolved in ethanol (300 ml), ammonium chloride is removed by filtration, and propylene oxide (9.5 g) is added. The mixture is kept in the refrigerator overnight, and the crude monohydrochloride is collected by filtration. It is dissolved in the minimum amount of water, filtered (millipore), and recrystallized by addition of 5–10 volumes of ethanol to give the title compound as the monohydrochloride, monohydrate (7.6 g).

Analysis for $C_6H_{13}FN_2O_2,HCl,H_2O$: Calculated: C, 32.96; H, 7.38; N, 12.81%. Found: C, 33.08; H, 7.23; N, 13.13%.

EXAMPLE 9

2-Fluoromethyl-2,6-diaminohexanoic acid (α-Fluoromethyl-lysine)

A. 4-Benzyloxybutanol

In a 2 l flask, a solution of 1,4-butanediol (45 g, 0.5 mol) and benzyl bromide (85.5 g, 0.5 mol) in dry THF (500 ml) is cooled to 0° C. (internal temperature). With vigorous stirring, potassium-tert-butoxide (56 g, 0.5 mol) is added in ~5 g portions, maintaining the internal temperature below 10° C. After addition of 1 N HCl (2 l), the mixture is saturated with sodium chloride, extracted with ether (1.5 l), washed with water, dried, and finally evaporated to give an oil (88 g) which is distilled under vacuum to give the pure title compound (63.5 g), bp₀.₂ 113°–114° C.

NMR (CDCl₃) δ: 1.65 (4H, m), 2.9 (1H, s), 3.53 (4H, m), 4.50 (2H, s), 7.33 (5H, s).

B. 1-Chloro-4-benzyloxybutane

A mixture of 4-benzyloxybutanol (64.8 g, 0.36 mol) in dry pyridine (200 ml) is stirred and heated to 50°–60° C. A solution of thionyl chloride (43 g, 0.36 mol) in pyridine (100 ml) is added slowly, and the mixture is kept at 60° C. for one more hour. After cooling to room temperature, the reaction mixture is poured into a mixture of ice and 2 N HCl. The mixture is saturated with sodium chloride, extracted with ether, and washed successively with water, 10% sodium bicarbonate, and water. Evaporation of solvent gives a yellow oil (49.7 g)

which is distilled under vacuum to give the pure title compound (47 g), bp$_{0.03-0.05}$ 85°–90° C.

NMR (CDCl$_3$) δ: 1.83 (4H, m), 3.88 (4H, m), 4.53 (2H, s), 7.37 (5H, s).

C. 2-Fluoromethyl-2-amino-6-benzyloxy-hexanenitrile

Under an atmosphere of nitrogen, the Grignard reagent is prepared from 1-chloro-4-benzyloxybutane (39.7 g, 0.2 mol), magnesium turnings (10 g, 0.4 mol), and dry ether (400 ml). The Grignard solution is separated from the excess of magnesium, transferred to a 2 l flask, and cooled to −40° C. A solution of fluoroacetonitrile (10.6 g, 0.18 mol) in ether (100 ml) is added slowly, the temperature being maintained between −40° and −30° C. Stirring is continued for 30 minutes more at this temperature. The reaction mixture is then poured into a vigorously stirred solution of sodium cyanide (39 g) and ammonium chloride (59 g) in water (200 ml) containing some ice (200 g). The mixture is vigorously stirred and allowed to warm up to room temperature during one hour. The organic phase is separated and extracted with 1 N HCl (2×250 ml). Basification with concentrated ammonia, extraction with ether, drying, and evaporation gives the title compound as a brown oil (28.3 g).

NMR (CDCl$_3$) δ: 1.63 (6H+2 NH$_2$, m+broad s), 3.48 (2H, m), 4.27 (2H, ABX, $J_{AB}=9$ Hz, $J_{AX}=J_{BX}=J_{H-F}=47$ Hz), 4.48 (2H, s), 7.33 (5H, s).

The product can be used for the next step without further purification.

D. 2-Fluoromethyl-2-phthalimido-6-benzyloxy-hexanenitrile

A solution of 2-fluoromethyl-2-amino-6-benzyloxy-hexanenitrile (28.3 g, 113 mol) and triethylamine (34.4 g) in dry dichloromethane (200 ml) is cooled in an ice bath, and a solution of phthaloyl dichloride (20.7 g) in dichloromethane (100 ml) is added slowly. After stirring at room temperature overnight, the solution is washed with 2 N HCl and with water. The solution is dried, treated with charcoal, and evaporated to give a brown oil (37 g). Flash chromatography on silica gel (1 kg, ether/petroleum ether 30:70) gives the pure title compound (16 g).

NMR (CDCl$_3$) δ: 1.70 (6H, m), 3.47 (2H, broadened t), 4.47 (2H, s), 5.07 (2H, ABX, $J_{AB}=9$ Hz, $J_{AX}=J_{BX}=J_{H-F}=47$ Hz), 7.32 (5H, s), 7.87 (4H, s).

E. 2-Fluoromethyl-2-phthalimido-6-hydroxy-hexanenitrile

A solution of 2-fluoromethyl-2-phthalimido-6-benzyloxy-hexanenitrile (15.5 g, 40.8 mmol) and trimethylsilyliodide (13 ml, 2.2 equivalents) in dry dichloromethane (100 ml) is stirred at room temperature under nitrogen overnight. After removing the solvent under vacuum, the residue is dissolved in dry chloroform, triethylamine (17 ml, 3 equivalents) is added, and the mixture is refluxed for 30 minutes. Upon cooling, the solution is stirred with 2 N HCl (250 ml) for 15 minutes, the phases are separated, and the organic layer is washed with sodium bicarbonate and with water. After evaporation, the residue is dissolved in THF and water (20 ml). Drops of 6 N HCl are added, and the resulting mixture is stirred for several minutes. The solvent is removed by evaporation, and the residue obtained is dissolved in chloroform, washed with water, and dried. Removal of solvent gives the crude title compound as an oil, (12 g). Chromatography on silica (300 g, eluent:ethylacetate) gives the pure material (9.0 g).

NMR (CDCl$_3$) δ: 1.25–2.0+2.0–3.0 (7H, 2 m), 3.57 (2H, broadened t), 5.03 (2H, ABX, $J_{AB}=9$ Hz, $J_{AX}=J_{BX}=J_{H-F}=46$ Hz), 7.80 (4H, s).

F. 2-Fluoromethyl-2-phthalimido-6-methanesulfonyloxy-hexanenitrile

A solution of 2-fluoromethyl-2-phthalimido-6-hydroxy-hexanenitrile (9.0 g, 31 mmol) and pyridine (60 ml) in dry dichloromethane (150 ml) is cooled in an ice bath, and methanesulfonyl chloride (3.6 g, 31 mmol), diluted with a small amount of dichloromethane, is added slowly with efficient stirring. Stirring is continued at room temperature overnight. The reaction mixture is washed with 2 N HCl and dried. Evaporation of solvent gives the title compound as a yellow oil (10.84 g).

NMR (CDCl$_3$) δ: 1.83 (6H, m), 3.00 (3H, s), 4.23 (2H, broadened t), 5.00 (2H, ABX, $J_{AB}=9$ Hz, $J_{AX}=J_{BX}=J_{H-F}=46$ Hz), 7.83 (4H, s).

G. 2-Fluoromethyl-2-phthalimido-6-iodo-hexanenitrile

2-Fluoromethyl-2-phthalimido-6-methanesulfonyloxy-hexanenitrile (10.84 g, 29.5 mmol) and sodium iodide (8.8 g, 2 equivalents) are refluxed in acetone overnight. The reaction mixture is filtered and solvent is removed by evaporation. The residue obtained is dissolved in ether and washed with water, sodium bisulfite, and water again. Upon concentration, the title compound crystallizes (9.0 g).

NMR (CDCl$_3$) δ: 1.4–2.6 (6H, m), 3.18 (2H, broadened t), 5.02 (2H, ABX, $J_{AB}=9$ Hz, $J_{AX}=J_{BX}=J_{H-F}=46$ Hz), 7.86 (4H, s).

H. 2-Fluoromethyl-2,6-diphthalimido-hexanenitrile

A mixture of 2-fluoromethyl-2-phthalimido-6-iodo-hexanenitrile (9.0 g, 22.5 mmol), dry DMF (30 ml), and potassium phthalimide (4.2 g, 1 equivalent) is stirred and heated at 80° C. for 4 hours. The DMF is removed under reduced pressure (0.1 mm Hg), and the residue is taken up in chloroform. The chloroform mixture is filtered, and the filtrate is washed with 2 N NaOH, 2 N HCl, and water. Evaporation of solvent gives a residue which, when dissolved in the minimum amount of acetone, crystallizes upon addition of ether. After standing at 5° C. overnight, the colourless crystals are collected (7.0 g), mp (Kofler) 136° C.

NMR (CDCl$_3$) δ: 1.2–3.0 (6H, m), 3.70 (2H, broadened t), 5.07 (2H, ABX, $J_{AB}=9$ Hz, $J_{AX}=J_{BX}=J_{H-F}=46$ Hz), 7.77+7.83 (8H, 2s).

I. 2-Fluoromethyl-2,6-diamino-hexanoic acid

2-Fluoromethyl-2,6-diphthalimido-hexanenitrile (5.0 g, 11.9 mmol) is refluxed with concentrated HCl for 14 hours. After addition of more concentrated HCl, heating is continued for 18 hours more. After the reaction mixture is cooled to room temperature, phthalic acid is removed by filtration, and the filtrate is evaporated to dryness. The residue is dissolved in water, treated with charcoal, and extracted three times with ether. Solvent is removed by evaporation. The residue is dried carefully (oil pump) and dissolved in dry ethanol. Ammonium chloride is removed by filtration, and the filtrate is treated with an excess of propylene oxide. After 2 hours at room temperature, the precipitate is removed by filtration and washed with ethanol and ether to give crude material (2.6 g). This material is dissolved in the minimum amount of water. The water solution is filtered (membrane filter) and upon addition of ethanol to the filtrate, the title compound crystallizes (1.0 g). A second crop (0.9 g) is obtained from the mother liquor. This second crop is recrystallized once more in the same manner. The total yield of pure title compound as the monohydrochloride: 1.50 g, mp 212° C.

Analysis for $C_7H_{15}FN_2O_2$, HCl: Calculated: C, 39.17; H, 7.51; N, 13.05%. Found: C, 39.33; H, 7.14; N, 13.04%.

NMR ($D_2O$/DCl) $\delta$: 1.2–2.3 (6H, m), 3.09 (2H, broad t), 4.91 (2H, ABX, $J_{AB}=10$ Hz, $J_{AX}=J_{BX}=J_{H-F}=46$ Hz).

EXAMPLE 10

2-Difluoromethyl-2-amino-5-benzyloxy-pentanenitrile

Under an atmosphere of nitrogen, 3-benzyloxypropyl-magnesium chloride is prepared from 1-chloro-3-benzyloxypropane (2.42 g, 13 mmol) in dry ether (13 ml) and magnesium turnings (660 mg, 26 mmol). The Grignard solution is separated from the excess of magnesium, cooled to −40° C., and a 10% solution of difluoroacetonitrile in dry THF (10 ml, 13 mmol) is added dropwise, maintaining the temperature at −40° C. After stirring at this temperature, for 30 minutes, the mixture is poured into a cold (0° C.) solution of sodium cyanide (1.27 g) and ammonium chloride (2.10 g) in water (40 ml). The mixture is stirred vigorously for 1 hour; during that time the reaction is allowed to warm up to room temperature. The organic phase is separated and extracted with 2 N HCl. Basification with concentrated ammonia (pH ~9–10), extraction with ether, drying, and evaporation gives the title compound as an oil (1.5 g).

NMR (CDCl$_3$) $\delta$: 1.90 (4H, +NH$_2$, m), 3.50 (2H, m), 4.48 (2H, s), 5.53 (1H, t, $J_{H-F}=56$ Hz), 7.30 (5H, s).

EXAMPLE 11

2-Fluoromethyl-2,5-diamino-4-oxo-valeric acid (α-Fluoromethyl-γ-oxo-ornithine)

A. 2-Fluoromethyl-2-amino-4-methyl-4-pentenenitrile

In a 10 l reactor, filled with nitrogen, about 100 ml of a solution of methallyl chloride (453 g, 490 ml, 5.0 mol) in dry tetrahydrofuran (THF) (4 l) is added to a stirred suspension of magnesium turnings (486 g, 20 mol) in tetrahydrofuran (THF) (1 l), previously activated by 2 ml of methyl iodide. The mixture is heated until Grignard formation starts. The reaction mixture is cooled with ice, and methallyl chloride solution is added at such a rate that the internal temperature does not exceed 50° C. After the reaction mixture is stirred overnight at room temperature, the Grignard reagent is separated from the excess of magnesium, transferred to a 20 l reactor, and cooled to −40° C. A solution of fluoroacetonitrile (276 g, 253 ml, 4.68 mol) in THF (1 l) is added slowly (within about 15 minutes), maintaining the internal temperature between −40° and −35° C. Stirring is continued for 30 minutes, at −40° C. The mixture is cooled to −60° C., and a water/THF mixture (300 ml, 1:1) is slowly added. A solution of ammonium chloride (795 g) and sodium cyanide (490 g) in water (7.5 l), previously cooled with ice, is added rapidly and the dry ice is removed. The mixture is stirred for 1 hour at an internal temperature between 0° C. and room temperature. The mixture is saturated with sodium chloride (about 2 kg), the organic layer is separated, and the aqueous phase is extracted twice with ether (2×3 l). The ether phase is dried (Na$_2$SO$_4$) and evaporated to give a dark oil (687 g) which is dissolved in ether (5 l) and extracted carefully with 10% hydrochloric acid (4×650 ml). The combined aqueous phases are cooled with ice and made basic with concentrated ammonia. The oil which separates is dissolved in diethyl ether (2.5 l), and the aqueous layer is extracted with diethyl ether (2×2 l). The combined ether extracts are dried (Na$_2$SO$_4$) and evaporated to afford the crude title compound as a dark oil (488 g).

NMR (CDCl$_3$) $\delta$: 1.93 (3H, s), 2.37 (2H, AB, $J_{AB}=13$ Hz), 4.33 (2H, ABX, $J_{AB}=8$ Hz, $J_{AX}=J_{BX}=J_{H-F}$), 5.0 (2H, m).

The product can be used for the next step without further purification.

B. 2-Fluoromethyl-2-phthalimido-4-methyl-4-pentenenitrile

In a 10 l reactor, equipped with a drying tube (CaCl$_2$), a solution of 2-fluoromethyl-2-amino-4-methyl-4-pentenenitrile obtained as in step A above (488 g, 3.44 mol) and triethylamine (685 g, 6.78 mol) in dry dichloromethane is cooled in an ice bath. A solution of phthaloyldichloride (625 g, 3.1 mol) in dichloromethane (1 l) is added slowly with stirring. After removal of the ice bath, the reaction mixture is stirred at room temperature overnight. The reaction mixture is washed with 2 N HCl hydrochloric acid (2×2 l) and then with water (2×2 l). The organic phase is dried (Na$_2$SO$_4$) and evaporated to give a residue. The residue is dissolved in dry dichloromethane (4 l), triethylamine (200 ml) is added, and the resulting mixture is refluxed for 4 hours (internal temperature 42° C.) Workup as described in Example 1 Step B gives an oil which solidifies on standing (773 g).

The solidified oil (60 g portions) is treated in a mortar with ethanol (45 ml). The mixture is filtered and washed with ethanol (15 ml) and twice with petroleum ether to give a yellow solid (427 g). The solid is dissolved in benzene (1.3 l) to which petroleum ether (2.2 l) is added. After several hours, more petroleum ether is added (1 l), and the mixture is kept at room temperature overnight. Filtration gives pure title material (349 g) (single spot by thin layer chromatography). A second crop is obtained by concentrating the mother liquor. The mother liquor obtained from the second crystallization is combined with the filtrate of the ethanol washings. Evaporation and chromatography on silica (2 kg, AcOEt/PE 20:80) gives an additional amount of pure material. Total yield: 471 g.

NMR (CDCl$_3$) $\delta$: 1.88 (3H, s), 2.98 (2H, AB, $J_{AB}=13$ Hz), 4.85 (2H, m), 5.17 (2H, ABX, $J_{AB}=9$ Hz, $J_{AX}=J_{BX}=J_{H-F}=46$ Hz), 7.80 (4H, s).

C. 2-Fluoromethyl-2-phthalimido-4-bromomethyl-4-pentenenitrile

2-Fluoromethyl-2-phthalimido-4-methyl-4-pentenenitrile obtained as in Step B above (12.38 g, 45.4 mmol), N-bromosuccinimide (8.11 g, 45.6 mmol), dry CCl$_4$ (100 ml), and a few mgs of benzoylperoxide are heated under reflux by irradiation with a lamp (375 W) for 4½ hours. Every hour, a few more mgs of benzoylperoxide are added. The reaction is monitored by NMR. After 4½ hours, less than 10% of starting material is left. After cooling to room temperature, succinimide is filtered off. The filtrate is washed with water (3×100 ml), dried (Na$_2$SO$_4$), and evaporated. The crude title compound is obtained as a solid (14.94 g).

NMR (CDCl$_3$) δ: 3.20 (2H, AB, J$_{AB}$=13 Hz), 4.10 (2H, AB, J$_{AB}$=11 Hz), 5.10 (1H, s), 5.13 (2H, ABX, J$_{AB}$=9 Hz, J$_{AX}$=J$_{BX}$=J$_{H-F}$=46 Hz), 5.37 (1H, s), 7.73 (4H, s).

The product can be used for the next step without further purification.

D. 2-Fluoromethyl-2-phthalimido-4-phthalimidomethyl-4-pentenenitrile

2-Fluoromethyl-2-phthalimido-4-bromomethyl-4-pentenenitrile obtained as in Step C above (14.94 g, 42.6 mmol), potassium phthalimide (7.90 g, 42.7 mmol) and dry dimethylformamide (DMF) (100 ml, refluxed over and distilled from calcium hydride), are heated (bath temperature 70°–80° C.) for 3 hours. The DMF is removed under vacuum (oil pump), the residue is dissolved in chloroform, salts are removed by filtration, and the filtrate is washed with 1 N sodium hydroxide and several times with water. The washed filtrate is dried (Na$_2$SO$_4$) and evaporated to give the crude title compound as a viscous oil. The oil is dissolved in chloroform (minimum amount). Equal volumes of diethyl ether and petroleum ether are added. Upon standing overnight, crystals (5.0 g) from oil are collected. The filtrate is evaporated, and the residue is chromatographed on silica (35 g/kg; AcOEt/PE 40:60). Total yield of pure title compound is 8.83 g.

NMR (CDCl$_3$) δ: 3.17 (2H, AB, J$_{AB}$=14 Hz), 4.33 (2H, s), 5.17 (2H, s with fine splitting), 5.23 (2H, ABX, J$_{AB}$=9 Hz, J$_{AX}$=J$_{BX}$=J$_{H-F}$=46 Hz), 7.82 (8H, s with fine splitting).

E. 2-Fluoromethyl-2,5-diphthalimido-4-oxo-pentanenitrile

A solution of 2.65 g (6.32 mmol) of 2-fluoromethyl-2-phthalimido-4-phthalimido methyl-4-pentenenitrile, obtained as in Step D above, in a 1:1 mixture (50 ml) of methylene chloride and methanol is cooled to −78° C. and treated with ozone (flow rate about 0.3 l/min) for 12¾ minutes (i.e 2 min/mol). An excess of dimethylsulfide (2 ml) is added, and the mixture is allowed to warm up to room temperature. After standing for 2 hours, the insoluble title ketone (1.73 g) is collected and washed with a small amount of chloroform and ether. The ketone is used for the next step without further purification. An analytical sample is obtained by recrystallization from hot tetrahydrofuran (100 ml/3.5 g)/CHCl$_3$ (100 ml).

Analysis for C$_{22}$H$_{14}$FN$_3$O$_5$: Calculated: C, 63.01; H, 3.37; N, 10.02%. Found: C, 62.91; H, 3.61; N, 10.03%.

F. 2-Fluoromethyl-2,5-diamino-4-oxo-valeric acid

2-Fluoromethyl-2,5-diphthalimido-4-oxo-pentanenitrile obtained as in Step E above (5.78 g, 13.8 mmol) is heated with concentrated hydrochloric acid (50 ml) at 100° C. (bath temperature) for 32 hours. After cooling to room temperature, phthalic acid is removed by filtration, and the filtrate is evaporated. The residue is dissolved in 1 N hydrochloric acid (50 ml) and extracted with ether (3×50 ml). After evaporation of the ether, the residue is dried carefully overnight (oil pump) and then dissolved in a 1:1 mixture of methanol and ethanol (80 ml). Ammonium chloride is removed by filtration and washed with the same mixture of methanol and ethanol. The washings are added to the original methanol/ethanol solution. Propylene oxide (3 ml) is added, and the mixture is kept at room temperature for several hours and then in the refrigerator overnight. The crude monohydrochloride which separates is collected, washed with a small amount of ethanol and ether, and dried (2.14 g). Treatment of the solid with charcoal in water at room temperature for 3½ hours and evaporation of water gives colourless material (2.11 g) which is recrystallized from water (15 ml) and ethanol. Drying at room temperature under vacuum (oil pump) in the presence of P$_2$O$_5$ gives the title compound as the monohydrochloride semihydrate (1.60 g), mp 154° C.

Analysis for C$_6$H$_{11}$FN$_2$O$_3$,HCl,½ H$_2$O: Calculated: C, 32.22; H, 5.86; N, 12.53%. Found: C, 32.25; H, 5.83; N, 12.48%.

NMR (D$_2$O/DCl) δ: 3.53 (2H, narrow AB, J$_{AB}$=18 Hz), 4.23 (2H, s), 4.87 (2H, d, J$_{H-F}$=46 Hz).

EXAMPLE 12

2-Fluoromethyl-2,5-diamino-4-oxo-valeric acid (α-Fluoromethyl-γ-oxo-ornithine)

A. 2-Fluoromethyl-2-amino-4-pentenenitrile

The Grignard reagent is prepared under an atmosphere of nitrogen, from magnesium turnings (19.1 g, 0.79 mol) and allyl chloride (60 g, 0.79 mol) in dry THF (800 ml). The reaction mixture is cooled to −30° C., and fluoroacetonitrile (30.2 g, 0.51 mol) in THF (100 ml) is added slowly. The mixture is then stirred for 30 more minutes at −30° C. The reaction mixture is then poured into a solution of sodium cyanide (50 g, 1.2 mol) and ammonium chloride (81 g, 1.53 mol) in water (1.1 l), and the mixture is stirred for 1 hour. After saturating the mixture with NaCl, the THF layer is separated and the aqueous phase is extracted with ether. Washing the ether layer with water and evaporation of solvent gives an oil (40 g), which is dissolved in ether and extracted with 2 N HCl. Basification with concentrated ammonia, re-extraction with ether, drying, and removal of the solvent gives the title compound as a brown oil (31.98 g).

NMR (CDCl$_3$)δ: 1.5–2.8 (2H+NH$_2$, m+broad s), 4.37 (2H, ABX, J$_{AB}$=10 Hz, J$_{AX}$=J$_{BX}$=J$_{H-F}$=47 Hz), 5.00–6.28 (3H, m).

This material is used for the next step without further purification.

B. 2-Fluoromethyl-2-amino-4-pentenoic acid

2-Fluoromethyl-2-amino-4-pentene nitrile (11.4 g, 89 mmol) is refluxed with concentrated HCl for 10 hours. After evaporation of the reaction mixture to dryness, the residue is dried carefully (oil pump). It is then dissolved in isopropanol (200 ml), ammonium chloride is removed by filtration, and the crude title compound is precipitated by addition of propylene oxide (15.5 g). Yield: 5.0 g.

NMR (D$_2$O/DCl)δ: 2.83 (2H, d with fine splitting), 5.00 (2H, ABX, J$_{AB}$=10 Hz, J$_{AX}$=J$_{BX}$=J$_{H-F}$=47 Hz), 5.3–6.0 (3H, m).

C. Methyl 2-fluoromethyl-2-amino-4-pentenoate

A mixture of 2-fluoromethyl-2-amino-4-pentenoic acid (3.83 g, 26 mmol), trimethylorthoformate (4.13 g, 39 mmol), and dry methanol (110 ml) is saturated with dry HCl gas with stirring and ice cooling. After the mixture is refluxed overnight, the solvent is evaporated to give the title compound as the hydrochloride (5.0 g).

NMR (D$_2$O/DCl)$\delta$: 2.83 (2H, d with fine splitting), 3.93 (3H, s), 4.97 (2H, ABX, J$_{AB}$=11 Hz, J$_{AX}$=J$_{BX}$=J$_{H-F}$=45 Hz), 5.45–6.2 (3H, m).

The free amino acid ester is obtained by dissolving the hydrochloride in a small amount of water, adjusting the pH to ~9 with sodium carbonate, saturating the solution with NaCl, and extraction with ether. From 4.62 g of the hydrochloride, 2.10 g of the free amino acid ester is obtained:

NMR (CDCl$_3$)$\delta$: 2.80 (2H, broadened d), 3.87 (3H, s), 4.87 (2H, d, J$_{H-F}$=46 Hz), 5,1–6.2 (3H, m).

D. Methyl 2-fluoromethyl-2-phthalimido-4-pentenoate

To a solution of methyl 2-fluoromethyl-2-amino-4-pentenoate (2.10 g, 13 mmol) and triethylamine (3 g) in dry dichloromethane, phthaloyl dichloride (2.37 g, 11.7 mmol) is added with ice cooling. After stirring overnight, at room temperature, the solution is washed with water and 1 N HCl. Drying and removal of solvent by evaporation gives a residue, consisting mainly of the iso-phthalimide. The residue is dissolved in dry dichloromethane, two equivalents of triethylamine are added, and the mixture is refluxed overnight. Work-up as described above gives the title compound as an oil (3.0 g).

NMR (CDCl$_3$)$\delta$: 3.17 (2H, broadened t, J=7 Hz), 3.77 (3H, s), 5.10 (2H, ABX, J$_{AB}$=9 Hz, J$_{AX}$=J$_{BX}$=J$_{H-F}$=47 Hz), 4.9–6.2 (3H, m), 7.77 (4H, s).

E. Methyl 2-fluoromethyl-2-phthalimido-3-carboxy-propionate

A solution of methyl 2-fluoromethyl-2-phthalimido-4-pentenoate (2.8 g, 9.6 mmol) and potassium permanganate (4.56 g, 29 mmol) in acetic acid (35 ml) and water (150 ml) is stirred at room temperature overnight. Sodium bisulfite is added to dissolve manganese dioxide. Saturation with NaCl, ether extraction, and evaporation of the solvent gives the title compound as a colourless oil which crystallizes on standing (2.10 g).

NMR (CDCl$_3$)$\delta$: 3.43 (2H, m), 3.80 (3H, s), 5.27 (2H, ABX, J$_{AB}$=9 Hz, J$_{AX}$=J$_{BX}$=J$_{H-F}$=47 Hz), 7.77 (4H, s).

F. Methyl 2-fluoromethyl-2-phthalimido-3-chlorocarbonyl-propionate

A solution of methyl 2-fluoromethyl-2-phthalimido-3-carboxy-propionate (2.37 g, 13.7 mmol) and pyridine (1.10 g, 13.7 mmol) in dry ether (50 ml) is treated with thionyl chloride (10 ml) at room temperature overnight. After addition of more ether (100 ml), pyridine hydrochloride is removed by filtration, and the solvent is evaporated to give the title compound as an orange oil (2.80 g).

NMR (CDCl$_3$)$\delta$: 3.80 (3H, s), 4.03 (2H, s), 5.23 (ABX, J$_{AB}$=9 Hz, J$_{AX}$=J$_{BX}$=J$_{H-F}$=47 Hz), 7.77 (4H, s).

G. Methyl 2-fluoromethyl-2-phthalimido-4-oxo-5-diazopentanoate

A solution of methyl 2-fluoromethyl-2-phthalimido-3-chlorocarbonyl-propionate (2.07 g, 6.33 mmol) in dry ether (24 ml) is slowly added with stirring to a cooled (ice) solution of diazomethane in ether (0.392 mol, 50 ml). After 30 minutes, the solvent is evaporated to give a yellow oil (2.1 g). This is purified by flash chromatography on silica gel (200 g, ethyl acetate/petroleum ether 4:6) to give the pure title compound as a yellow oil (1.7 g);

NMR (CDCl$_3$)$\delta$: 3.33 (2H, AB, J$_{AB}$=16 Hz, additional fine splitting, ~1.5 Hz), 3.80 (3H, s), 5.27 (2H, ABX, J$_{AB}$=9 Hz, J$_{AX}$=J$_{BX}$=J$_{H-F}$=47 Hz), 5.40 (1H, s), 7.77 (4H, s).

H. Methyl 2-fluoromethyl-2-phthalimido-4-oxo-5-bromo-pentanoate

A solution of methyl 2-fluoromethyl-2-phthalimido-4-oxo-5-diazo-pentanoate (1.53 g, 4.62 mmol) in ether (22.5 ml) is added dropwise and with vigorous stirring to cold (ice cooling) aqueous HBr (47%, 0.95 ml). Stirring is continued for 1 hour at room temperature. The organic phase is separated, washed with water, dried, and evaporated to give the title compound as a yellow oil (1.52 g).

NMR (CDCl$_3$)$\delta$: 3.66 (2H, s with fine splitting), 3,80 (3H, s), 4.07 (2H, s), 5.20 (2H, ABX, J$_{AB}$=9 Hz, J$_{AX}$=J$_{BX}$=J$_{H-F}$=47 Hz), 7.75 (4H, s).

I. 2-Fluoromethyl-2,5-diamino-4-oxo-valeric acid

A mixture of methyl 2-fluoromethyl-2-phthalimido-4-oxo-5-bromo-pentanoate (1.42 g, 3.69 mmol), potassium phthalimide (820 g, 4.4 mmol) in dry DMF (5 ml) is heated at 70° C. for 3 hours. The solvent is removed under vacuum (oil pump), and the residue is refluxed with concentrated HCl for 32 hours. Work-up and propylene oxide precipitation as described previously gives the crude title product as the monohydrochloride (540 mg).

EXAMPLE 13

2-Fluoromethyl-2-amino-3-(4'-imidazolyl)propionic acid (α-Fluoromethylhistidine)

A. 2-Fluoromethyl-2-amino-3-[4'-(2'-mercapto)-imidazolyl]-propionic acid

A solution of 2-fluoromethyl-2,5-diamino-4-oxo-hexanoic acid monohydrochloride semihydrate (60.0 g, 0.268 mol) and potassium thiocyanate (140 g, 1.44 mol) in water (67 ml) is stirred and heated at 100° C. for 3 hours. The mixture is then allowed to cool to room temperature and kept at 5° C. for several hours. The title compound is collected and washed with water, ethanol, and ether. Yield 43.03 g. This material, mp 271° C. (dec.) is used for the next step without further purification.

NMR (D$_2$O/DCl)$\delta$: 3.53 (2H, s), 5.06 (2H, ABX, J$_{AB}$=11 Hz, J$_{AX}$=J$_{BX}$=J$_{H-F}$=45 Hz), 7.23 (1H, s).

B. 2-Fluoromethyl-2-amino-3-(4'-imidazolyl)-propionic acid

A solution of 2-fluoromethyl-2-amino-3-[4'-(2'-mercapto)]-propionic acid (43.03 g, 0.196 mol) and ferric chloride (159.5 g, 0.984 mol) in 2 N HCl (100 ml) and water (2 l) is heated for 2 hours (bath temperature: 110° C.). The reaction mixture is cooled to room temperature, sodium acetate trihydrate (535 g) and water (2 l) are added, and the solution is saturated with hydrogen sulfide. After filtration and carefully washing with water, the filtrate is acidified strongly with concentrated HCl and evaporated to dryness. The residue is dissolved in concentrated HCl (2 l). Sodium chloride is removed by filtration and washed with concentrated HCl (3×500 ml). Solvent is removed and the residue is dissolved in water (1.4 l). Concentrated ammonia is added until a pH 9-10 (~30 ml) is achieved. After addition of more ammonia (10 ml), the solution is saturated with hydrogen sulfide again. After filtration, the solution is acidified (HCl) to precipitate some sulfur, which is removed by filtration through a membrane filter (Millipore). At this stage, the solution is tested qualitatively for the absence of ferrous and ferric ions (oxidation and thiocyanate testing).

Solvent is removed by filtration, and the residue is dissolved in water (1.4 g). A 20% aqueous solution of barium chloride is added in portions until the supernatant gives a precipitate with sodium sulfate solution (total amount of BaCl$_2$-solution=190 ml). After removing BaSO$_4$ by filtration, concentrated HCl is added, and the solution is evaporated to dryness. The residue is dried carefully overnight under vacuum (oil pump). It is then dissolved in dry ethanol (1.2 l). Ammonium chloride (and excess barium chloride) are removed from the solution by filtration. Crude α-fluoromethylhistidine, monohydrochloride, is precipitated by addition of propylene oxide (40 ml). Systematic work-up of the mother liquors (evaporation with HCl, reprecipitation with propylene oxide) gives a total of 36.9 g of crude material which, according to NMR, retains some ethanol. This material is dissolved in water, treated with charcoal (10 weight-%) at room temperature and crystallized by addition of isopropanol to give 16.33 g of product. A second recrystallization (5% charcoal) gives a first crop (10.51 g) of pure title compound. More pure material is obtained by systematic work-up: mother liquors of the first crystallization are converted to the di-hydrochloride and re-precipitated with propylene oxide; mother liquors of the second crystallization are treated with charcoal and recrystallized from water (1.7 times the weight of compound) and isopropanol. Total yield of pure title compound as the monohydrochloride is 21 g, mp 218° C. (dec.).

Analysis for $C_7H_{10}FN_3O_2$,HCl: Calculated: C, 37.59; H, 4.96; N, 18.79%. Found: C, 37.42; H, 4.74; N, 18.87%.

NMR (D$_2$O/DCl)δ: 3.40 (2H, s), 4.80 (2H, ABX, $J_{AB}$=11 Hz, $J_{AX}$=$J_{BX}$=$J_{H-F}$=46 Hz), 7.37 (1H, s), 8.56 (1H, s).

What is claimed is:

1. A process for preparing a compound of the formula:

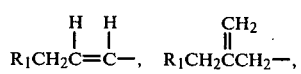

wherein:
p is 1 or 2 and
R is:

$$R_1CH_2C\overset{H}{=}\overset{H}{C}-, \quad R_1CH_2C\overset{CH_2}{\|}CH_2-,$$

$R_2OCH_2CH_2CH_2-$, $R_2OCH_2CH_2CH_2CH_2-$, $R_3CH_2-$, or $CH_2=CHCH_2-$, wherein:
R$_1$ is hydrogen, methoxy, benzyloxy, diphenylmethoxy, triphenylmethoxy, or allyloxy;
R$_2$ is methyl, benzyl, diphenylmethyl, triphenylmethyl, or allyl; and R$_3$ is a substituted-phenyl group of the formula:

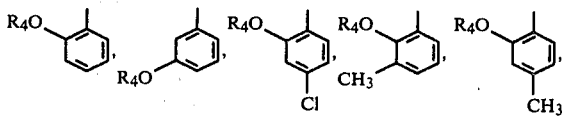

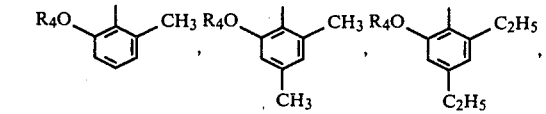

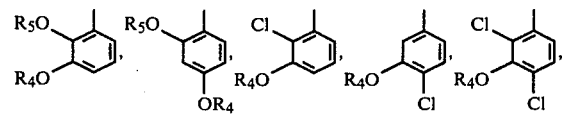

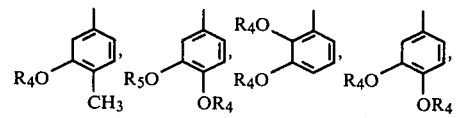

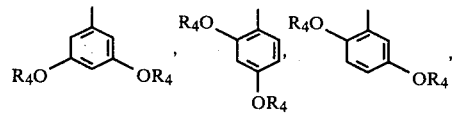

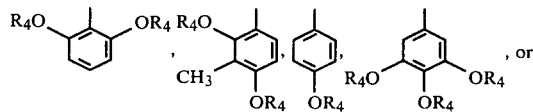

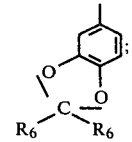

wherein R$_4$ is (C$_1$-C$_8$)alkyl, R$_5$ is benzyl, and R$_6$ is hydrogen or methyl; with the proviso that when R is R$_3$CH$_2$— wherein R$_3$ is

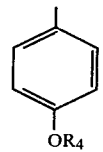

p cannot be 2;

which comprises treating a ketimine magnesium halide of the formula:

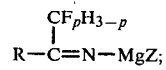

wherein R and p have the meanings hereinabove defined and Z is chloride, bromide, or iodide; with hydrogen cyanide or with an alkali metal cyanide or ammonium cyanide and a proton source of sufficient acidity to form the corresponding imine from said ketimine magnesium halide.

2. A process as defined in claim 1 wherein the ketimine magnesium halide is treated with an alkali metal cyanide or ammonium cyanide and a proton source.

3. A process as defined in claim 2 wherein the proton source is an ammonium salt of a strong acid.

4. A process as defined in claim 3 wherein the proton source is ammonium chloride.

5. A process as defined in claim 1 wherein the ketimine magnesium halide is treated with sodium cyanide and ammonium chloride.

6. A process as defined in claim 1, 2, 3, 4, or 5 wherein R is

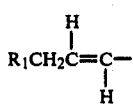

wherein $R_1$ is hydrogen, methoxy, benzyloxy, diphenylmethoxy, triphenylmethoxy, or allyloxy.

7. A process as defined in claim 6 wherein R is

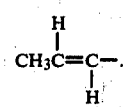

8. A process as defined in claim 1, 2, 3, 4, or 5 wherein R is $R_2OCH_2CH_2CH_2$— wherein $R_2$ is methyl, benzyl, diphenylmethyl, triphenylmethyl, or allyl.

9. A process as defined in claim 8 wherein R is $CH_3OCH_2CH_2CH_2$— or

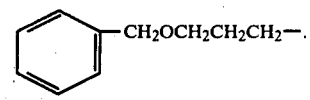

10. A process as defined in claim 1, 2, 3, 4, or 5 wherein R is $R_2OCH_2CH_2CH_2CH_2$— wherein $R_2$ is methyl, benzyl, diphenylmethyl, triphenylmethyl, or allyl.

11. A process as defined in claim 10 wherein R is $CH_3OCH_2CH_2CH_2CH_2$— or

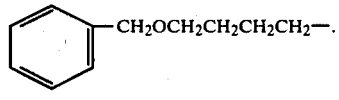

12. A process as defined in claim 1, 2, 3, 4, or 5 wherein R is $R_3CH_2$— wherein $R_3$ is a substituted-phenyl group of the formula:

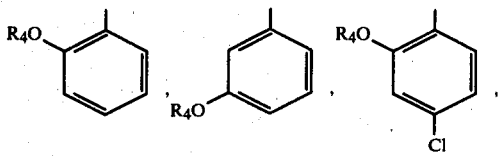

-continued

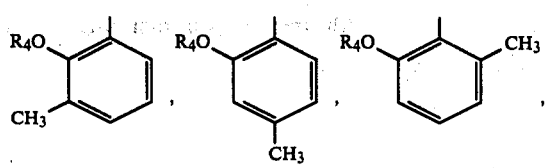

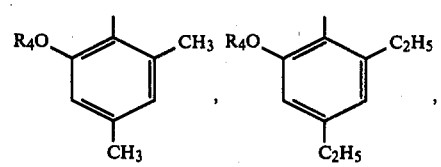

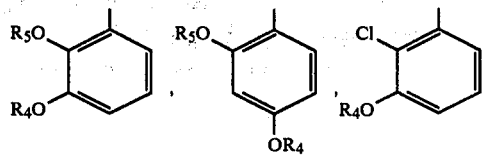

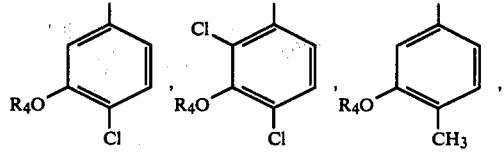

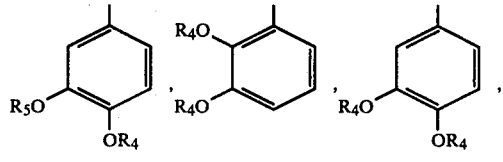

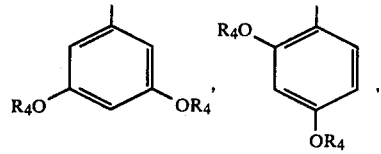

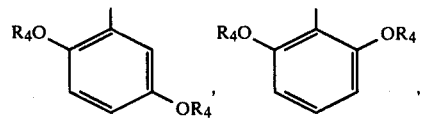

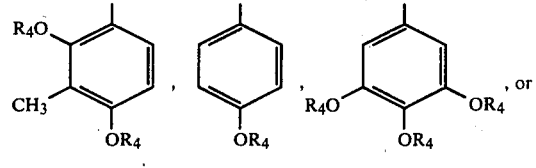

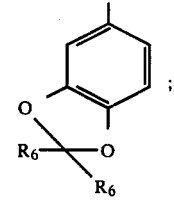

wherein R₄ is C₁–C₈ alkyl, R₅ is benzyl, and R₆ is hydrogen or methyl; with the proviso that when R is R₃CH₂— wherein R₃ is

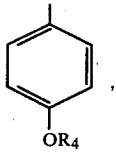

p cannot be 2.

13. A process as defined in claim 12 wherein R₄, as defined by R₃, is methyl and R₅ is benzyl.

14. A process as defined in claim 10 wherein R₃ is:

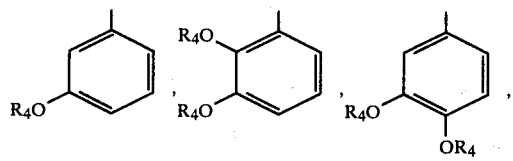

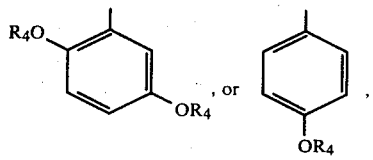

wherein R₄ is C₁–C₈ alkyl.

15. A process as defined in claim 14 wherein R₄ is methyl.

16. A process as defined in claim 1, 2, 3, 4, or 5 wherein R is $$R_1CH_2\overset{\overset{\displaystyle CH_2}{\|}}{C}CH_2-$$

wherein R₁ is hydrogen, methoxy, benzyloxy, diphenylmethoxy, triphenylmethoxy, or allyloxy.

17. A process as defined in claim 16 wherein R is $$CH_3\overset{\overset{\displaystyle CH_2}{\|}}{C}CH_2-.$$

18. A process as defined in claim 1, 2, 3, 4, or 5 wherein R is CH₂=CHCH₂—.

* * * * *

UNITED STATES PATENT AND TRADEMARK OFFICE
CERTIFICATE OF CORRECTION

PATENT NO. : 4,405,530

DATED : September 20, 1983

INVENTOR(S) : Fritz E. Gerhart

It is certified that error appears in the above-identified patent and that said Letters Patent are hereby corrected as shown below:

At column 8, line 12, the patent reads "nitrile groups" and should read --nitrile group--.

At column 10, line 18, the patent reads "diamino-nitrle" and should read --diamino-nitrile--.

At column 15, line 40, the patent reads "1964]. the" and should read --1964]. The--.

At column 15, line 62, the patent reads "describe" and should read --described--.

At column 19, line 54, the patent reads "1.66 mmol" and should read --166 mmol--.

At column 20, line 1, the patent reads "J = 7H$_z$" and should read --J-7H$_z$--.

At column 28, lines 8 and 9, the patent reads "$J_{AX}=J_{BX}J_{H-F}=46H_z$" and should read --$J_{AX}=J_{BX}=J_{H-F}=46H_z$--.

At column 29, line 14, the patent reads "$J_{AB}=90H_z$," and should read --$J_{AB}=9$ H$_z$,--.

At column 30, Example 8H, the title is missing and should read -- 2-Fluoromethyl-2,5-diaminovaleric acid --.

UNITED STATES PATENT AND TRADEMARK OFFICE
CERTIFICATE OF CORRECTION

PATENT NO. : 4,405,530

DATED : September 20, 1983

INVENTOR(S) : Fritz E. Gerhart

It is certified that error appears in the above-identified patent and that said Letters Patent are hereby corrected as shown below:

At column 38, line 19, the patent reads "3,80" and should read --3.80--.

At column 41, line 35, the patent reads "$CH_3OCH_2CH_2CH_2-$" and should read -- $CH_3OCH_2CH_2CH_2$ --.

Signed and Sealed this

Fifth Day of April, 1988

Attest:

DONALD J. QUIGG

Attesting Officer

Commissioner of Patents and Trademarks